United States Patent
Smolko et al.

(10) Patent No.: US 7,107,783 B2
(45) Date of Patent: Sep. 19, 2006

(54) SELF-COOLING CONTAINERS FOR LIQUIDS

(75) Inventors: Daniel D. Smolko, Jamul, CA (US); Gregory J. Kevorkian, Temecula, CA (US)

(73) Assignee: Advanced Porcus Technologies, LLC, San Diego, CA (US)

( * ) Notice: Subject to any disclaimer, the term of this patent is extended or adjusted under 35 U.S.C. 154(b) by 301 days.

(21) Appl. No.: 10/453,863

(22) Filed: Jun. 3, 2003

(65) Prior Publication Data

US 2004/0007553 A1 Jan. 15, 2004

Related U.S. Application Data

(63) Continuation-in-part of application No. 10/162,119, filed on Jun. 3, 2002, which is a continuation of application No. 08/933,639, filed on Sep. 19, 1997, now Pat. No. 6,398,048.

(60) Provisional application No. 60/458,054, filed on Mar. 25, 2003, provisional application No. 60/404,355, filed on Aug. 16, 2002, provisional application No. 60/388,609, filed on Jun. 3, 2002.

(51) Int. Cl.
- B65B 63/08 (2006.01)
- F28C 1/00 (2006.01)
- F28D 5/00 (2006.01)
- F28D 3/08 (2006.01)

(52) U.S. Cl. ............... 62/315; 62/316; 62/60; 62/371

(58) Field of Classification Search ............... 62/304, 62/315, 316, 60, 457.3, 457.4, 371
See application file for complete search history.

(56) References Cited

U.S. PATENT DOCUMENTS

| | | | |
|---|---|---|---|
| 296,432 A * | 4/1884 | Moebius | 62/312 |
| 921,387 A | 5/1909 | Etter | |
| 1,465,497 A * | 8/1923 | Tandy | 62/316 |
| 2,435,033 A | 1/1948 | Campbell | |
| 3,051,993 A | 9/1962 | Goldman et al. | |
| 3,083,861 A | 4/1963 | Amberg et al. | |
| 3,326,401 A | 6/1967 | De Long | |
| 3,362,186 A * | 1/1968 | Patterson | 62/316 |
| 3,696,958 A | 10/1972 | Lee | |
| 3,768,682 A | 10/1973 | Meyers et al. | |
| 3,915,752 A | 10/1975 | Gross | |
| 3,938,695 A | 2/1976 | Ruff | |
| 4,076,656 A | 2/1978 | White et al. | |

(Continued)

FOREIGN PATENT DOCUMENTS

CH 658 901 A5 12/1985

(Continued)

OTHER PUBLICATIONS

U.S. Appl. No. 10/162,119, filed Jun. 3, 2002.

(Continued)

*Primary Examiner*—William C. Doerrler
(74) *Attorney, Agent, or Firm*—G. L. Loomis & Associates, Inc.; Gary L. Loomis

(57) ABSTRACT

Disclosed are self-cooling containers for beverages and other liquids. Such containers comprise porous matrices as elements of the container bodies to effect the cooling of contained liquids by pervaporation. The liquid vapor can pass through the porous matrix directly to the environment or to a collector or trap comprising an absorbent material in contact with the container. Also disclosed are self-cooling containers incorporating insulative sleeves that reduce radiative warming of container surfaces yet permit sufficient pervaporative flux to cool containers residing within such sleeves.

47 Claims, 15 Drawing Sheets

U.S. PATENT DOCUMENTS

| | | | | |
|---|---|---|---|---|
| 4,147,841 | A | 4/1979 | Shroff | |
| 4,271,977 | A | 6/1981 | Saigne | |
| 4,368,766 | A * | 1/1983 | Nomi | 383/80 |
| 4,380,157 | A * | 4/1983 | Christiani | 62/315 |
| 4,489,844 | A | 12/1984 | Breskin | |
| 4,560,077 | A | 12/1985 | Dutt | |
| 4,618,071 | A | 10/1986 | Vincent | |
| 4,623,070 | A | 11/1986 | Nishikawa | |
| 4,648,519 | A | 3/1987 | Kennedy | |
| 4,746,035 | A | 5/1988 | Anderson et al. | |
| 4,761,232 | A | 8/1988 | Bright | |
| 4,765,499 | A | 8/1988 | Von Reis et al. | |
| 4,778,601 | A | 10/1988 | Lopatin et al. | |
| 4,828,772 | A | 5/1989 | Lopatin et al. | |
| 4,838,464 | A | 6/1989 | Briggs et al. | |
| 4,865,207 | A | 9/1989 | Joyner et al. | |
| 4,925,068 | A | 5/1990 | Schneider | |
| 4,934,545 | A | 6/1990 | Pezzoli et al. | |
| 4,938,395 | A | 7/1990 | Jamieson | |
| 4,946,080 | A | 8/1990 | Vesborg | |
| 4,967,941 | A | 11/1990 | Beck et al. | |
| 5,018,635 | A | 5/1991 | Whittaker | |
| 5,025,945 | A | 6/1991 | Lyon | |
| 5,040,703 | A | 8/1991 | Roark et al. | |
| 5,104,008 | A | 4/1992 | Crisci | |
| 5,135,124 | A | 8/1992 | Wobser | |
| 5,143,614 | A | 9/1992 | Soria et al. | |
| 5,184,740 | A | 2/1993 | Mandrell, II et al. | |
| 5,238,569 | A | 8/1993 | Soria et al. | |
| 5,242,079 | A | 9/1993 | Stephens et al. | |
| 5,259,522 | A | 11/1993 | Morton | |
| 5,262,444 | A | 11/1993 | Rusincovitch et al. | |
| 5,265,777 | A | 11/1993 | Weinstein | |
| 5,282,540 | A | 2/1994 | Beck | |
| 5,328,063 | A | 7/1994 | Beck et al. | |
| 5,337,971 | A | 8/1994 | Rohrig | |
| 5,353,949 | A | 10/1994 | Seibert et al. | |
| 5,429,255 | A | 7/1995 | Glynn | |
| 5,465,876 | A | 11/1995 | Crisci | |
| 5,472,120 | A | 12/1995 | Stebick et al. | |
| 5,480,054 | A | 1/1996 | Midden | |
| 5,497,920 | A | 3/1996 | Moeller et al. | |
| 5,509,551 | A | 4/1996 | Terrell, II | |
| 5,531,338 | A | 7/1996 | Sklar | |
| 5,542,670 | A | 8/1996 | Morano | |
| 5,662,247 | A | 9/1997 | Rapchak et al. | |
| 5,693,273 | A | 12/1997 | Wolbrom | |
| 5,725,645 | A | 3/1998 | Wickland et al. | |
| 5,727,707 | A | 3/1998 | Wickland et al. | |
| 5,743,444 | A | 4/1998 | Beck et al. | |
| 5,804,074 | A | 9/1998 | Takiguchi et al. | |
| 5,810,185 | A | 9/1998 | Groesbeck | |
| 5,811,038 | A | 9/1998 | Mitchell | |
| 5,819,973 | A | 10/1998 | Traub, Sr. et al. | |
| 5,850,908 | A | 12/1998 | Jasek | |
| D405,693 | S | 2/1999 | Bretz et al. | |
| 5,875,909 | A | 3/1999 | Guglielmini | |
| 5,894,962 | A | 4/1999 | Song et al. | |
| 5,897,037 | A | 4/1999 | Mann | |
| 5,901,867 | A | 5/1999 | Mattson | |
| 5,946,931 | A * | 9/1999 | Lomax et al. | 62/304 |
| 5,975,369 | A | 11/1999 | Yurkewicz et al. | |
| 5,988,426 | A | 11/1999 | Stern | |
| 5,988,448 | A | 11/1999 | Foth | |
| 5,992,635 | A | 11/1999 | Walters | |
| 6,006,952 | A | 12/1999 | Lucas | |
| 6,024,012 | A | 2/2000 | Luzenberg, Jr. | |
| 6,041,982 | A | 3/2000 | Cautereels et al. | |
| 6,116,446 | A | 9/2000 | Haughton et al. | |
| 6,116,458 | A | 9/2000 | Dark | |
| 6,135,329 | A | 10/2000 | Stoneberg et al. | |
| 6,182,464 | B1 * | 2/2001 | Mamich | 62/316 |
| 6,202,871 | B1 | 3/2001 | Kelly | |
| 6,202,901 | B1 | 3/2001 | Gerber et al. | |
| 6,274,181 | B1 | 8/2001 | Richison et al. | |
| 6,276,543 | B1 | 8/2001 | German et al. | |
| 6,282,913 | B1 * | 9/2001 | Moriguchi et al. | 62/259.2 |
| 6,290,090 | B1 | 9/2001 | Essebaggers | |
| 6,298,554 | B1 | 10/2001 | Fuchs | |
| 6,389,839 | B1 | 5/2002 | Sabin | |
| 6,398,048 | B1 | 6/2002 | Kevorkian et al. | |
| 6,454,137 | B1 | 9/2002 | Sturk | |
| 6,474,515 | B1 | 11/2002 | Ladina et al. | |
| 2001/0018096 | A1 | 8/2001 | Klare | |
| 2002/0056695 | A1 | 5/2002 | Boulange et al. | |
| 2002/0074366 | A1 | 6/2002 | Young | |
| 2002/0112499 | A1 * | 8/2002 | Goldfine | 62/316 |

FOREIGN PATENT DOCUMENTS

| | | |
|---|---|---|
| DE | 3902 233 A1 | 1/1989 |
| EP | 0 414 098 A2 | 8/1990 |
| EP | 0635 436 A2 | 7/1994 |
| FR | 2 736 329 A1 | 7/1995 |
| WO | WO 00/34132 A2 | 6/2000 |
| WO | WO 00/34132 A3 | 6/2000 |

OTHER PUBLICATIONS

U.S. Appl. No. 10/453,864, filed Jun. 3, 2002.

PCT International Search Report for Application No. PCT/US03/17544.

* cited by examiner

FIG. 3C
FIG. 3D
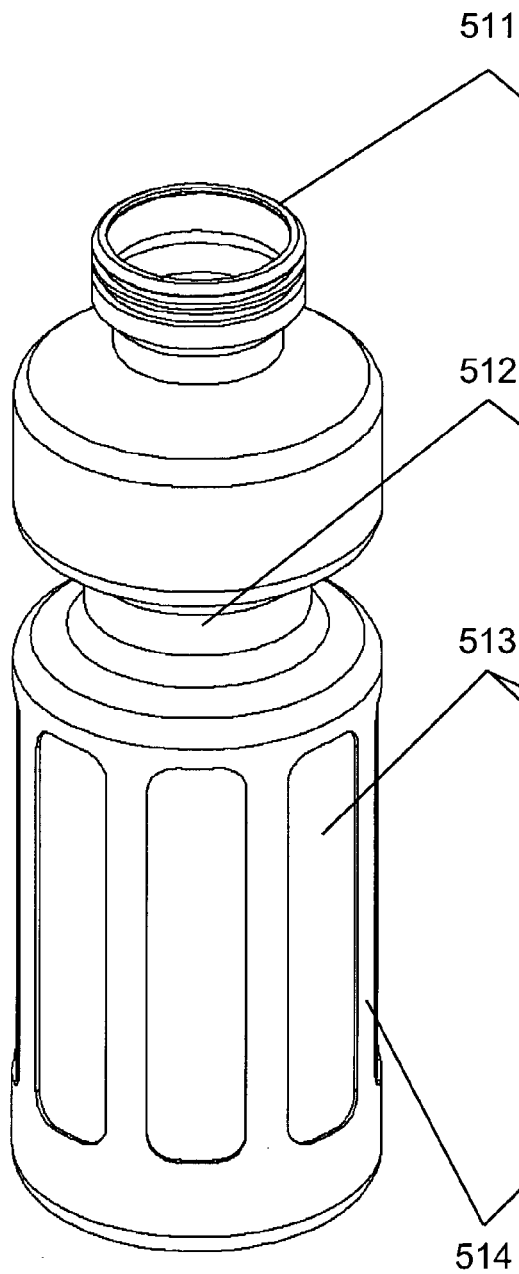
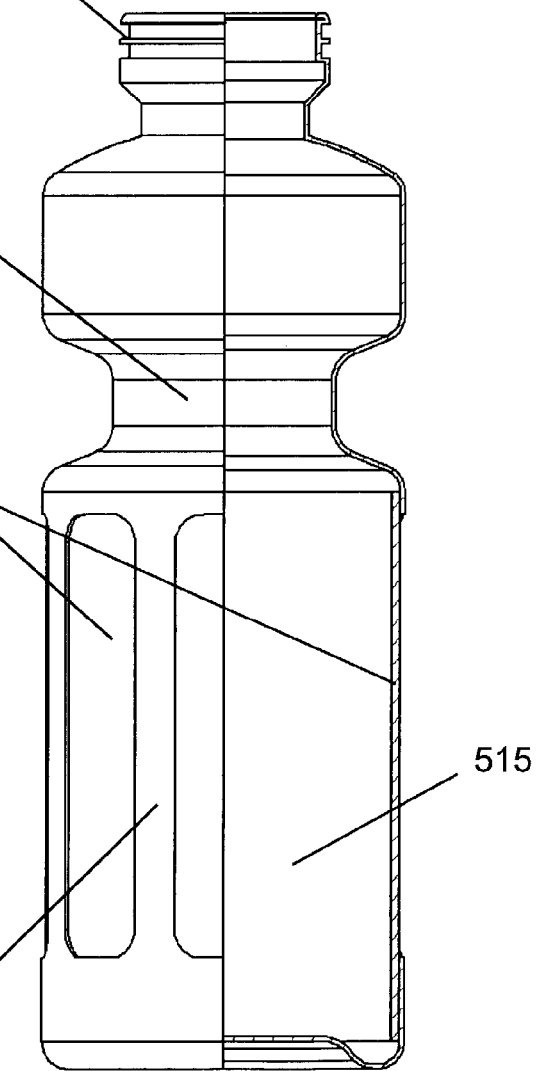

FIG. 4
FIG. 5
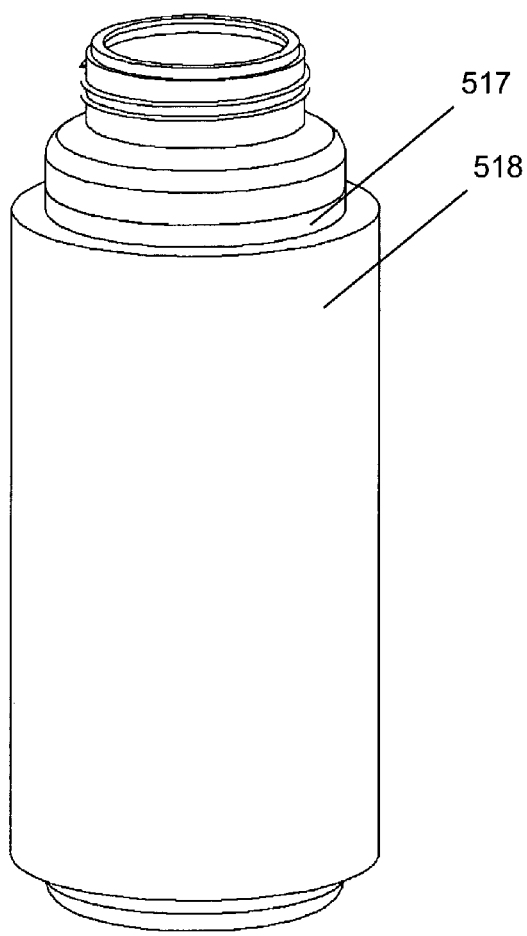
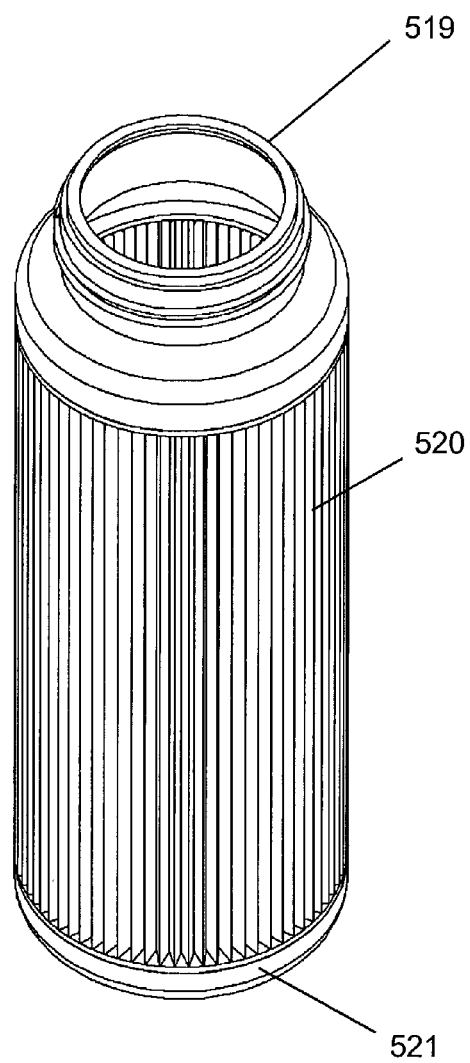

FIG. 6A
FIG. 6B
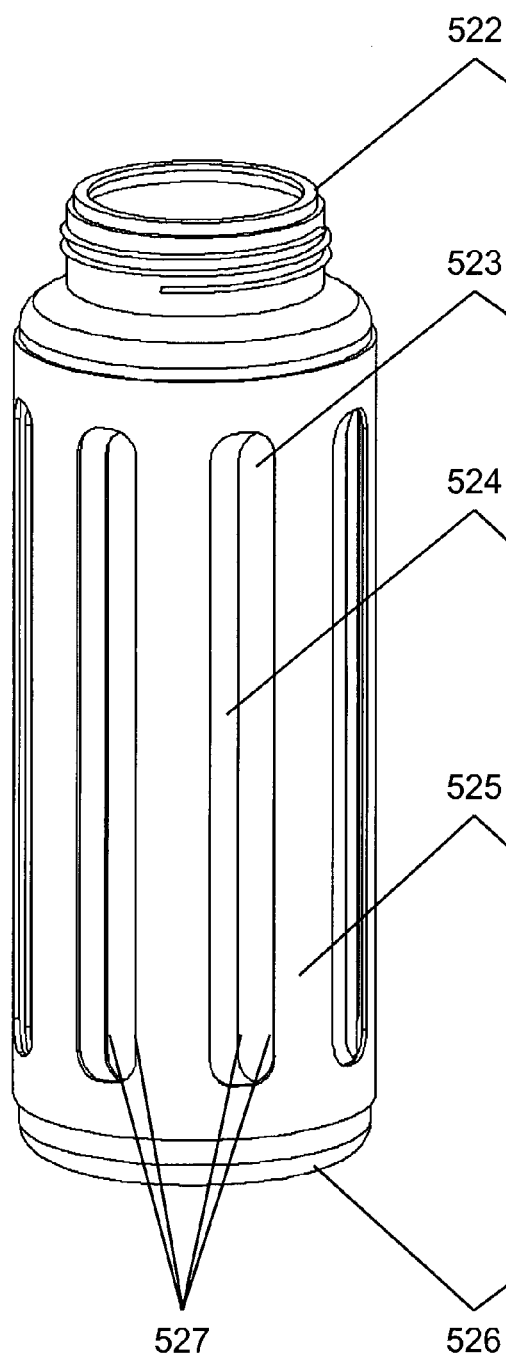
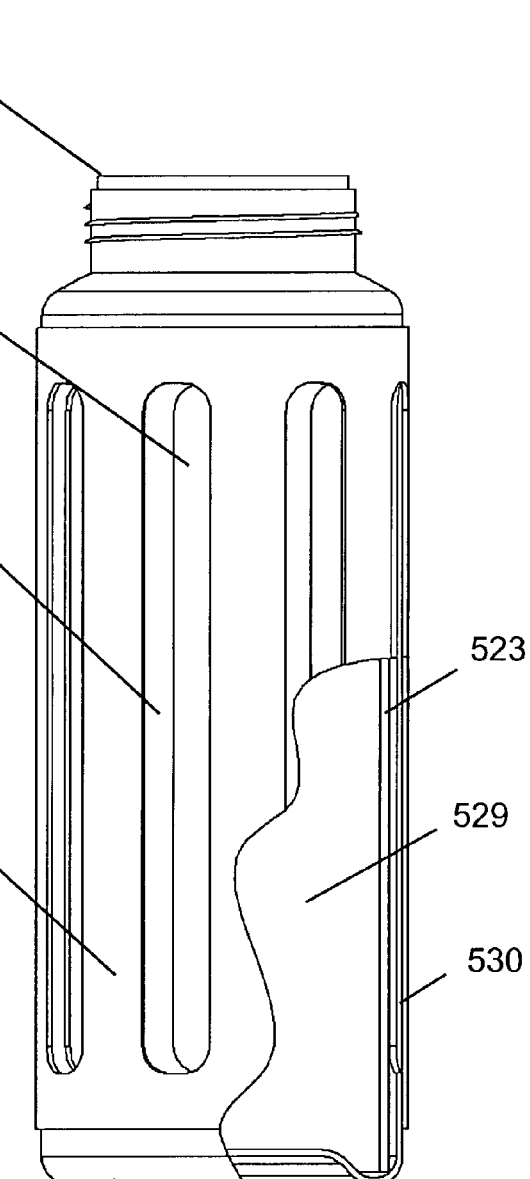

FIG. 7
FIG. 8
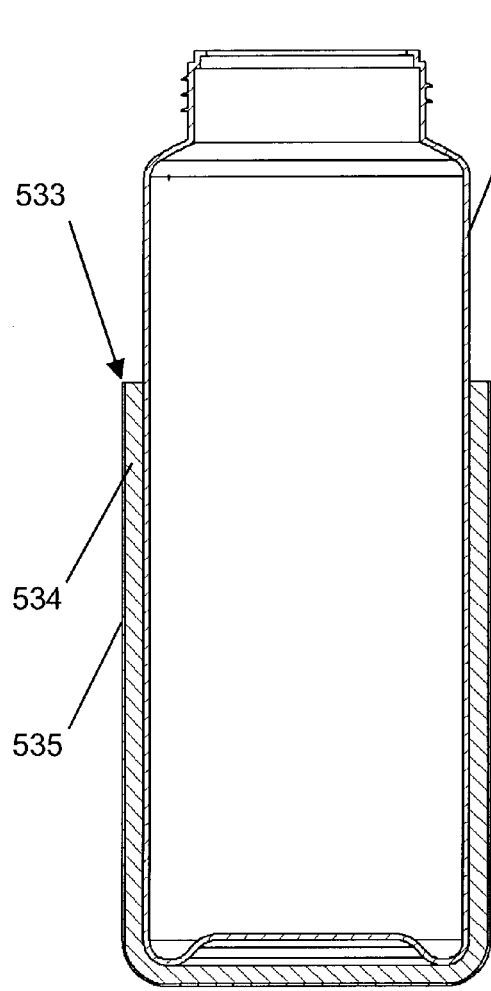
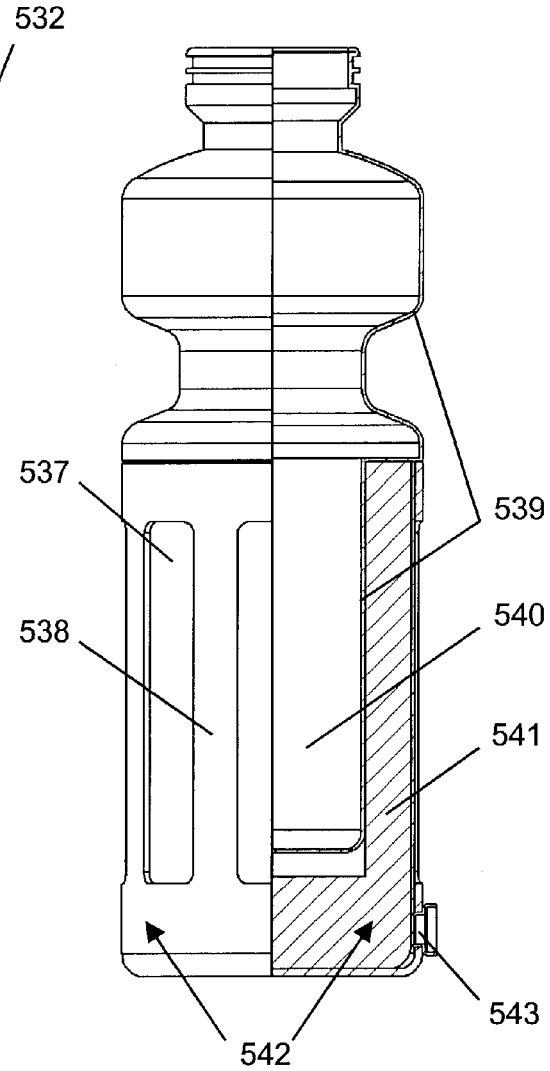

SELF-COOLING CONTAINERS FOR LIQUIDS

RELATED APPLICATION DATA

This application claims priority under 35 U.S.C. § 119(e) to U.S. Provisional Application Ser. No. 60/388,609, filed Jun. 3, 2002, and is also a continuation-in-part of U.S. patent application Ser. No. 10/162,119, filed Jun. 3, 2002, which is a continuation of U.S. patent application Ser. No. 08/933,639 filed Sep. 19, 1997, now U.S. Pat. No. 6,398,048, the disclosures of which are hereby incorporated by reference in their entireties. This application further claims priority to U.S. Provisional Application Ser. Nos. 60/404,355, filed Aug. 16, 2002, and 60/458,054, filed Mar. 25, 2003.

BACKGROUND OF THE INVENTION

1. Field of the Invention

This invention relates to a device and method of construction of a container or closure used to cool a liquid by means of pervaporation.

2. Description of the Related Art

Evaporative cooling of both dwellings and water originated in Ancient Egypt and subsequently spread eastward through the Middle-East and Iran, to the north of India, westward across north Africa to southern Spain and other regions suffering from a hot and dry climate. In the initial use of this process non-glazed clay pots were used for centuries for the storage of water with the added side benefit of cooling the liquid water contents by absorbing and wicking the water to the outer clay surface followed by the evaporation of the water from this surface. Unfortunately, evaporation directly from the outer clay surface eventually lead to scale formation and reduced cooling efficiency as the minerals build up on this surface reducing the liquid permeability and lowering the liquid vapor pressure.

Other methods based on heat transfer reduction from the environment to the liquid have been used. Methods that have been used include vacuum and air gap thermoses, and foam insulative jackets. Additional devices using ice, frozen cold packs or sticks have been used to compensate for heating by surrounding environment and the return of the liquid in the container to ambient temperature. In all these cases the design of the system necessitates that either the liquid contents, a separate chamber and/or the shell of the bottle be cooled which can lead to excessive weight issues in addition to a liquid volume displacement loss in the container. In all of these methods the temperature of the liquid will equilibrate and eventually return to the ambient temperature.

Pervaporation (PV) is defined as a combination of matrix vapor permeation and evaporation. From 1987 on, membrane pervaporation has gained wide acceptance by the chemical industry for the separation and recovery of liquid mixtures (Chemical Engineering Progress, pp. 45–52, July 1992). The technique is characterized by the introduction of a barrier matrix between a liquid and a gaseous phase. A liquid is in intimate contact with one side of the matrix. Mass transfer of vapor occurs selectively to the gas side of the matrix resulting in the loss of liquid or the loss of select volatile liquid components and the loss of evaporative latent heat. The process is termed pervaporation because of the unique combination of vapor "permeation" through the porous matrix and the liquid to vapor phase change "vaporization". Without heat added to the liquid, the temperature falls due to the latent heat of vaporization until an equilibrium temperature is reached where the heat absorbed from the environment is equal to the latent heat lost due to liquid evaporation at the matrix surface or within the pores.

U.S. Pat. No. 5,946,931 illustrates the use of an evaporative cooling PTFE membrane device using a stream of fluid in a laminar flow profile above a membrane in order to cool an attached device or environment. U.S. Pat. No. 4,824,741 illustrates the use of a pervaporative cooling matrix to cool the surface of the plate of an electrochemical cell. The moist plate may be made from uncatalyzed PTFE-bonded electrode material, a suitable porous sintered powder, porous fibers, or even a porous polymer film. U.S. Pat. No. 4,007,601 demonstrates the use of evaporative cooling in a circulating porous hollow heat exchanger to obtain a cooled fluid.

SUMMARY OF THE INVENTION

Disclosed herein is a simplified pervaporative cooling system for beverage and liquid containers that does not use any mechanical pumps to supply liquid to the pervaporative matrix surface and does not rely on a vacuum to enhance the cooling efficiency as in the above prior art. A container is defined as any apparatus or enclosure that holds liquid whether it is open or closed to the external environment. In one embodiment, this approach utilizes a pervaporative matrix that preferably forms part of the container body or housing and comprises between 5 to 100% of the total surface area of the container. The liquid contents of the container are then cooled directly at the surrounding liquid/membrane interface due to the latent heat of evaporation of the water. The resulting liquid vapor is lost through the matrix to the surrounding environment or to a collector or trap such as may comprise an absorbent material. Preferred containers include bottles, jars, carboys, and pouches. The containers may, in some embodiments, be fabricated into larger structures, including housings, dispensers, and garments.

In one embodiment, there is provided a pervaporatively cooled container, comprising a container body comprising one or more walls, wherein at least a portion of said one or more walls comprises a pervaporative matrix, said matrix comprising a porous hydrophobic material, wherein said matrix allows for the passage of small quantities of molecules of a volatile liquid vapor through the matrix, the evaporation of which cools the container, including any contents of the container. In one embodiment, there is provided a pervaporatively cooled tube or straw, comprising an elongate hollow tubular structure comprising an outer pervaporative layer comprising a hydrophobic material coextensive with a porous internal layer comprising a hydrophilic material, the internal layer defining a lumen through which a liquid can pass. In one embodiment, the tubular structure is formed from a hydrophobic porous tube in which the inner surface of the tube has been chemically treated to be hydrophilic, thus forming the internal layer.

In one embodiment, there is provided a cooling jacket for a container, comprising a jacket body comprising an outer layer comprising a hydrophobic porous material; and an inner layer coextensive with said outer layer and in fluid communication with said outer layer, said inner layer being adapted to hold a volatile liquid wherein said jacket body is shaped to allow the inner layer to contact at least a portion of a container.

In a preferred embodiments, the containers and cooling jackets may further comprise a regenerable or disposable outer layer, directly adjacent to or in contact with the pervaporative layer, comprising a desiccant, absorbent material or other substance that absorbs or adsorbs the moisture or other fluid resulting from pervaporation.

In one embodiment, there is provided a cooling garment comprising at least two layers: an outer layer comprising a pervaporative material comprising a hydrophobic pervaporative laminate; an optional middle layer comprising a thin support liquid barrier layer for the pervaporative layer; and an inner layer; wherein the outer layer is in fluid communication with a body of coolant liquid, and the inner layer is in thermal contact with the wearer of the garment. The wearer of the garment is cooled by the pervaporation of the coolant liquid through the pervaporative material of the outer layer. In a preferred embodiment, the cooling garment is incorporated or integrated into a piece of clothing such as a protective garment or suit. The garment may further comprise a tube in fluid communication with the body of coolant liquid which allows the wearer of the garment to orally consume coolant liquid, preferably water. In a preferred embodiment, the garment further comprises a regenerable or disposable outer layer comprising a desiccant or an absorbent material that absorbs the moisture or other fluid resulting from pervaporation.

In preferred embodiments, one or more of the following may also be present: the garment is in thermal contact either by direct contact with the skin or contact through a piece of fabric or material, such fabric or material being worn by the wearer of the garment and/or being part of the garment itself; the outer layer is pleated to increase surface area for pervaporation; the middle layer is a barrier to potentially hazardous biological or chemical materials; and the inner layer comprises patterned or serpentine regions formed by a heat sealing process.

In a related embodiment, the garment may further comprise or be in fluid communication with a reservoir holding additional coolant liquid. The coolant can be fed into the interstices formed between the pervaporative matrix and the middle layer from the reservoir by gravity or by wicking. Preferred coolant liquids comprise water, alcohols, and blends thereof.

In related embodiments, containers such as bottles or backpacks comprising pervaporative material, as described below, are also provided.

BRIEF DESCRIPTION OF THE DRAWINGS

FIGS. 3A, 3B, 3C and 3D, illustrates plan and cut away views of embodiments in which support ribs enhance the rigidity of a porous matrix.

FIG. 4 shows a container comprising an outer porous insulative layer. This sleeve reduces direct radiative warming of the inner bottle surface, yet allows for the pervaporative flux and loss of latent heat.

FIG. 5 illustrates one embodiment of container comprising a pleated matrix which serves as a method for increasing the effective cooling surface area of the container. This allows for a higher surface area and quicker liquid cool down time for the container.

FIGS. 6A and 6B show one embodiment of a container in plan and cutaway view comprising an adjustable sleeve to limit the extent of pervaporative flux and liquid loss from the container. This sleeve preferably also reduces direct radiative warming of the inner bottle surface, yet allows for the pervaporative flux and loss of latent heat.

FIG. 7 illustrates a cross section of a two-layer pervaporative sleeve comprising a sponge or sponge-like material that can be used with a container.

FIG. 8 shows a cutaway view of another embodiment of pervaporative cooling jacket that is used on a central housing containing a liquid, such as a carbonated beverage.

Figures 1A, 1B:
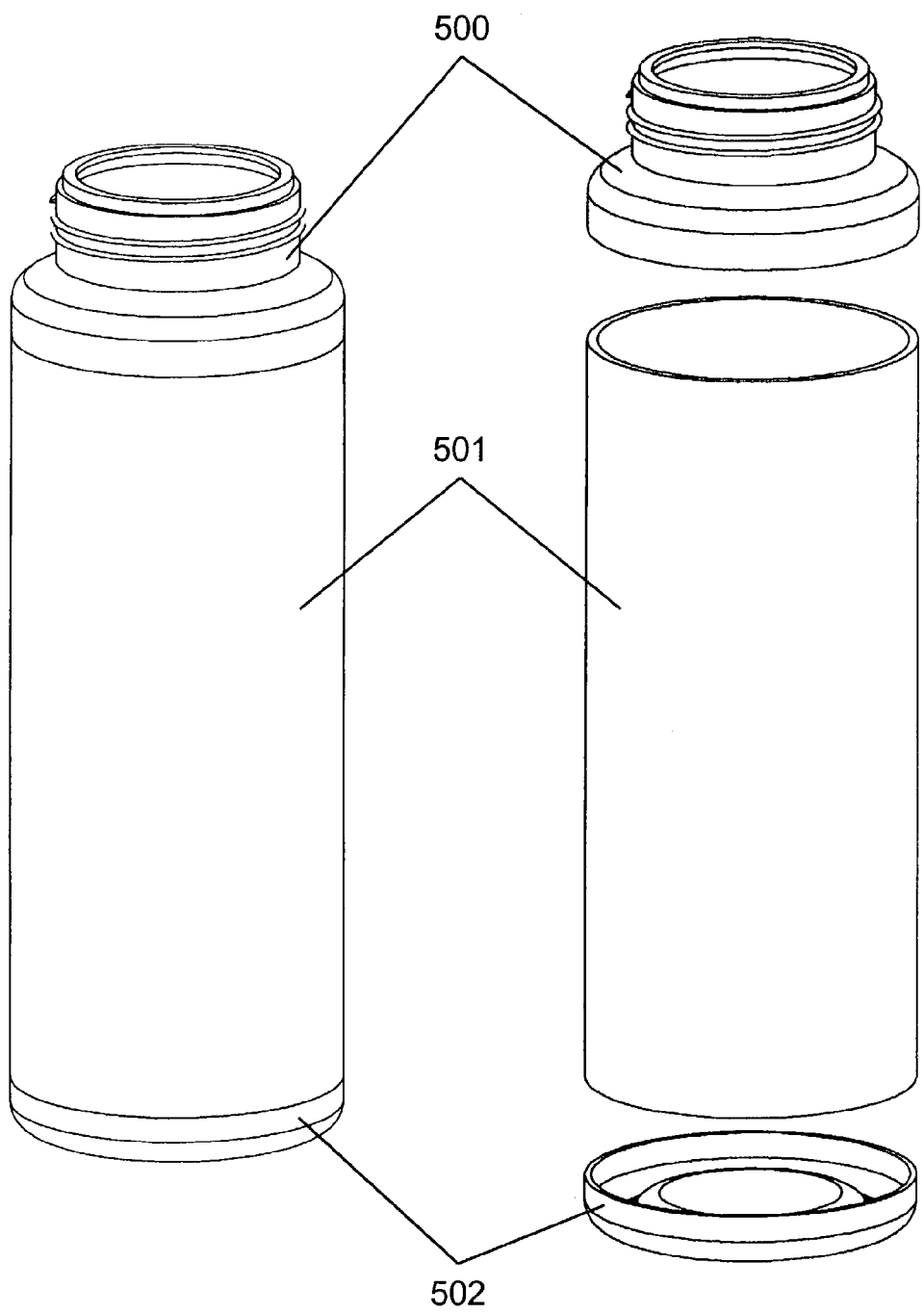
FIGS. 1A and 1B illustrate a bottle in plan and exploded view in which a generally planar porous matrix may be wrapped around or pushed over a bottle body as a cylinder.

The figures illustrate preferred embodiments and are intended to be merely exemplary and representative of certain embodiments. To that end, several figures contain optional features that need not be included in any particular embodiment of the invention, and the shape, type, or particular configuration of container or closure illustrated should not be taken as limiting on the invention.

DETAILED DESCRIPTION OF THE PREFERRED EMBODIMENTS

Disclosed herein are containers and enclosures that use pervaporative cooling to cool a liquid or item residing in such container or enclosure. In preferred embodiments, the containers are comprised of porous vent materials, also called porous matrices. In one embodiment the container forms part of a pervaporative cooling garment.

Porous matrices may be made of any of a wide variety of materials, including, but not limited to, plastics, elastomers, metals, glass, and ceramics. Combinations of plastics, elastomers, metals, glasses, or ceramics may also be used. The combinations may be intimate, such as from blending of two or more components to become co-sintered, or may be layered, such as from laminate structures derived from two or more materials. Combinations of different plastics, elastomers, metals, glasses, or ceramics can also be co-sintered or fabricated into laminate structures for use in pervaporative containers. Preferred plastics for porous vent materials include, but are not limited to thermoplastic polymers, thermoset elastomers, and thermoplastic elastomers. Preferred thermoplastic polymers include, but are not limited to, low density polyethylene (LDPE), linear low density polyethylene (LLDPE), medium density polyethylene (MDPE), high-density polyethylene (HDPE), ultra-high molecular weight polyethylene (UHMWPE), polypropylene (PP) and its copolymers, polymethylpentene (PMP), polybutylene terephthalate (PBT); polyethyleneterephthalate (PET), polyethyleneterephthalate glycol modified (PETG), polyetheretherketone (PEEK), ethylenevinylacetate (EVA), polyethylenevinylalcohol (EVOH), polyacetal, polyacrylonitrile (PAN), poly(acrylonitrile-butadiene-styrene) (ABS), poly(acrylonitrile-styrene-acrylate) (AES), poly(acrylonirile-ethylene-propylene-styrene) (ASA), polyacrylates, polymethacrylates, polymethylmethacrylate (PMMA), polyvinylchloride (PVC), chlorinatedpolyvinylchloride (CPVC), polyvinyldichloride (PVDC) fluorinated ethylenepropylene (FEP), polyvinylfluoride (PVF), polyvinylidinefluoride (PVDF), polytetrafluoroethylene (PTFE), polyester, cellulosics, polyethylenetetrafluoroethylene (ETFE), polyperfluoroalkoxyethylene (PFA), nylon 6 (N6), polyamide, polyimide, polycarbonate, polyetheretherketone (PEEK), polystyrene (PS), polysulfone, and polyethersulfone (PES). Preferred thermoset elastomers include styrene-butadiene, polybutadiene (BR), ethylene-propylene, acrylonitrile-butadiene (NBR), polyisoprene, polychloroprene, silicone, fluorosilicone, urethanes, hydrogenated nitrile rubber (HNBR), polynorborene (PNR), butyl rubber (IIR) to include chlorobutyl (CIIR) and bromobutyl (BIIR), fluoroelastomers such as Viton® and Kalrez®, Fluorel™, and chlorosulfonated polyethylene. Preferred thermoplastic elastomer (TPE) categories include thermoplastic olefins (TPO) including those commercially available as Dexflex® and Indure®; elastomeric PVC blends and alloys; styrenic block copolymers (SBC) including styrene-butadiene-styrene (SBS), styrene-isoprene-styrene (SIS), styrene-ethylene/butylene-styrene (SEBS), and styrene-ethylene-propylene-styrene (SEPS), some commercially available SBCs include those sold under the trademarks Kraton®, Dynaflex®, and Chronoprene™; thermoplastic vulcanizate (TPV, also known as dynamically vulcanized alloys) including those commercially available under the trademarks Versalloy®, Santoprene®, and Sarlink®; thermoplastic polyurethane (TPU) including those commercially available under the trademarks ChronoThane®, Versollan™, and Texrin®; copolyester thermoplastic elastomers (COPE) including those commercially available as Ecdel®; and polyether block copolyamides (COPA) including those commercially available under the trademark PEBAX®. Preferred metals for porous materials include stainless steel, aluminum, zinc, copper and its alloys. Preferred glass and ceramics for porous materials include quartz, borosilicate, aluminosilicate, sodiumaluminosilicate, preferably in the form of sintered particles or fibers derived from said materials.

A preferred method of making macroporous plastic is by a process called sintering, wherein powdered or granular thermoplastic polymers are subjected to the action of heat and pressure to cause partial agglomeration of the granules and formation of a cohesive macroporous sheet or part. The macroporous material comprises a network of interconnected macropores that form a random tortuous path through the sheet. Typically, the void volume or percent porosity of a macroporous sheet is from 30 to 65% depending on the conditions of sintering although it may be greater or lesser than the stated range depending on the specific method of manufacturer. Due to the adjustment of chemical or physical properties, the surface tension of a macroporous matrix can be tailored to repel or absorb liquids, but air and vapors can readily pass through. For example, U.S. Pat. No. 3,051,993 to Goldman, herein incorporated by reference in its entirety, discloses the details of making a macroporous plastic from polyethylene.

Porous plastics, including macroporous plastics, suitable for making a pervaporatively-cooled container in accordance with preferred embodiments, can be manufactured in sheets or molded to specification and is available for purchase from a number of sources. Porex Corporation (Fairbum, Ga., U.S.A.) is one such source, and provides porous plastic under the trademark, POREX®. Porous plastic sold under the name POREX® can be purchased in sheets or molded to specification from any one of the thermoplastic polymers previously described. The average porosity of such POREX® materials can vary from about 1 to 350 microns depending on the size of polymer granules used and the conditions employed during sintering. GenPore® (Reading, Pa., U.S.A.) is another manufacturer of porous plastic products, with pore sizes ranging from 5 to 1000 microns. MA Industries Inc. (Peachtree City, Ga., U.S.A.) also manufactures porous plastic products. Porvair Technology Ltd (Wrexham North Wales, U.K.) is another manufacturer of porous products supplying both porous plastic (range of 5 to 200 um pore size under brand name Vyon™) and porous metal media (under brand name Sinterflo®).

The basic size, thickness and porosity of the plastic chosen to make a pervaporative matrix may be determined by calculating the amount of vapor that must pass through the vent in a given period of time (flow rate) and the heat transfer rate from the environment back into the liquid. The flux rate (flow rate per unit area) of a given macroporous plastic varies depending on factors including the pore size, percent porosity, and cross sectional thickness of the matrix and is generally expressed in terms of volume per unit time per unit area. To achieve a sufficient degree of pervaporative cooling, the flow rate of vapor through the matrix should be such that the thermodynamic heat removed from the liquid initially at room temperature due to vaporization is greater than the heat absorbed from the environment. During the, pervaporative process the container liquid temperature cools until the heat loss of the liquid due to vaporization of the liquid contents through the matrix matches the heat gain from the surrounding environment.

In common usage, "Macroporosity" generally refers to the overall void volume of a material or its macrostructure. The term "Macroporous" is generally used to classify a material's individual pores that are considered large in size. The term "Microporosity" generally refers to the individual pore sizes or distribution of pore sizes that constitute the microstructure of a porous material. The term "Microporous" is generally used to classify a material's individual pores that are considered small in size. For purposes of the disclosure herein, pore size (diameter) is classified according to the International Union of Pure and Applied Chemistry (IUPAC) Subcommittee of Macromolecular Terminology, definitions of terms drafted on Feb. 26, 2002. This standard divides pore size classification into three categories: Microporous (<0.002 μm), Mesoporous (0.002 to 0.050 μm) and Macroporous (>0.050 μm). Also for the purposes of this disclosure herein, void volume will be discussed in terms of the "Percent Porosity" of the material. Both macroporous as well as mesoporous materials with pore sizes of 0.05 μm or less can be used for pervaporative cooling. Preferred methods for fabrication include casting or stretching membranes of such materials.

Preferred porous materials include those in which the pores on opposite surfaces (what will become the interior and exterior surfaces) are interconnected such that the two sides are in communication with each other. Such interconnections are preferably not, however, straight through as to create a single cylindrical tube through which material passes; instead a network of pores creates a tortuous path.

For a single layer pervaporative matrix, the porous materials are preferably macroporous with pore sizes greater than or equal to 0.05 μm, preferably about 0.1 to 500 μm, and about 0.5 to 10 μm, including 0.25, 0.5, 1, 5, 15, 20, 40, 60, 80, 100, 150, 200, 250, 300, 350, 400, and 450 μm. In one embodiment, the matrix materials used in conjunction with the pervaporative containers are between 0.1 and 100 μm, preferably between 0.5 and 75 μm. The percent porosity (percent open area) of the materials are preferably about 10 to 90%, preferably 30 to 75% or 50 to 70%, including 20%, 40%, 60%, and 80%. The thickness of the porous materials preferably ranges from 0.025 to 7 mm, including between 1 and 3 mm. Preferred thickness for matrix materials used in pervaporative containers are about 0.05 to 5 mm and about 0.1 to 3.0 mm, including 0.2, 0.3, 0.5, 0.7, 1.0, 1.25, 1.5, 1.75, 2.0, and 2.5 mm. Other embodiments may have values for the above parameters that are above or below those set forth above. For single layer matrices, it is preferred that the material be hydrophobic or have a hydrophobic coating. For the values set forth in this paragraph, as well as elsewhere in the specification, the stated ranges include as the values contained in between the values specifically mentioned. In other embodiments, materials can have one or more properties having values lying outside the disclosed ranges.

The matrix material can be derived from plastic, elastomers, glass, metal, or combinations thereof. Some preferred matrix materials, including thermoplastic polymers, thermoset elastomers, thermoplastic elastomer, metals, glass and ceramics are as detailed above. Matrix materials may be purchased from commercial sources, or they may be made according to a variety of techniques. U.S. Pat. No. 4,076,656 to White et al. details one technique in which porogens are added to molten or dissolved materials, which can be leached out with a solvent, or extracted with supercritical fluids after the material sets and is in its final form. U.S. Pat. No. 5,262,444 to Rusincovitch et al. details another technique to create porous material by introducing porogens that evolve into gases after processing a material, to leave behind a porous structure. These patents are hereby incorporated by reference in their entireties.

Although many pervaporative matrix materials discussed herein are hydrophobic, oleophobic pervaporative materials may also be used when the pervaporation liquid is an organic liquids such as alcohol. Commodity plastic materials such as nylon, polysulfone, and the cellulosics, are available in hydrophilic grades. These hydrophilic materials can be milled into particles and sintered using techniques known to those familiar in the art to produce hydrophilic porous materials with high liquid flux rates. Porous hydrophilic plastic, including macroporous plastic can be manufactured in sheets or molded to specification and is available for purchase from a number of sources, including Porex Corporation. Porous hydrophilic fiber materials can range in pore size from 20 to 120 μm with percent porosity ranging from 25 to 80 for the pore volume. Moreover, hydrophobic porous materials can be rendered hydrophilic by one or more treatment processes familiar to those skilled in the art including, but not limited to, plasma etching, chemical etching, impregnation with wetting agents, or application of hydrophilic coatings. In addition, a masking process can be used in conjunction with one or more treatment processes to selectively pattern a hydrophobic porous material with regions of hydrophilicity with high liquid flux rates, if desired.

For example, multilayered porous constructs containing two or more layers of porous material. Thin layers can be laminated to make thicker layers using techniques familiar to those in the art. Multilayered constructs may be used to obtain a mechanical and physically superior matrix as previously observed in our tests. For instance, combining a sintered macroporous matrix of polyethylene with a thin layer of expanded PTFE on the liquid side of the container increases the hydrophobicity and liquid breakthrough pressure of water from 5 psi to over 30 psi, yet the layered matrix still maintains a similar pervaporative flux to that obtained using porous polyethylene by itself. Thickness of laminates preferably ranges from about 0.025 to 7000 μm with average pore sizes, percent porosity and other properties preferably as described above.

Pervaporative matrix materials may also be derived from porous materials made from blends. In a preferred embodiment, the porous materials comprise a fluorinated resin, including, but not limited to, polyvinylfluoride (PVF), polyvinylidinefluoride (PVDF), polytetrafluoroethylene (PTFE), polyethylenetetrafluoroethylene (ETFE), fluorinated ethylene propylene (FEP), polyperfluoroalkoxyethylene (PFA), and/or fluorinated additives such as Zonyl®, blended with selected polyolefin or other resins, preferably those selected from the series of polyethylenes (LLDPE, LDPE, MDPE, HDPE, UHMWPE) polypropylene, polyesters, polycarbonates, ABS, acrylics, styrene polymethylpentene (PMP), polybutylene terephthalate (PBT); polyethyleneterephthalate (PET), polyetheretherketone (PEEK), ethylenevinylacetate (EVA), polyacetal, poly(acrylonitrile-butadiene-styrene) (ABS), poly(acrylonitrile-styrene-acrylate) (AES), poly(acrylonirile-ethylene-propylene-styrene) (ASA), polyesters, polyacrylates, polymethacrylates polymethylmethacrylate (PMMA), polyvinylchloride (PVC), polyvinyldichloride (PVDC) nylon 6 (N6), polyamide, polyimide, polycarbonate, polystyrene, and polyethersulfone (PES). Elastomers may also be used alone or in blends. Preferred elastomers include those of the thermoset type such as styrene-butadiene, polybutadiene (BR), ethylene-propylene, acrylonitrile-butadiene (NBR), polyisoprene, polychloroprene, silicone, fluorosilicone, urethanes, hydrogenated nitrile rubber (HNBR), polynorborene (PNR), butyl rubber (IIR) to include chlorobutyl (CIIR) and bromobutyl (BIIR). The resulting blends, including sintered blends, have porous structures with varying amounts of porosity, flexibility and mechanical strength determined predominately from the non-PTFE or other non-fluorinated resin, and high water intrusion pressures determined predominately from the fluorinated resin due to its preferential migration to the pore surface during the sintering process. The percent porosity, pore size, and thickness are preferably as noted above. Blended matrix materials may be purchased from commercial sources, or they may be made according to a variety of techniques. U.S. Pat. No. 5,693,273 to Wolbrom details a process of cosintering to produce multi-porosity porous plastic sheets that can be derived from two or more polymeric resin materials and U.S. Pat. No. 5,804,074 to Takiguchi et al. et al. details a process to produce a plastic filter by cosintering two or more polymeric resins in a molding process to produce filter parts. Both of these patents are hereby incorporated by reference into this disclosure in their entirety.

Pervaporative Cooling

In preferred embodiments, a simplified pervaporative cooling system for containers is presented that does not use any mechanical pumps to supply liquid to the pervaporative matrix surface and does not rely on a vacuum to enhance the cooling efficiency. The present approach utilizes a pervaporative matrix that forms part of the container, preferably the housing of the container, and comprises between about 5 to 100% of the total surface area of the container, including about 10%, 20%, 30%, 40%, 50%, 60%, 70%, 80%, and 90% of the total surface area. The liquid contents of the container are preferably cooled directly at the surrounding liquid/matrix interface due to the latent heat of evaporation of the liquid, such as water or a water/dissolved solid mixture or solution, in the container. In an alternate embodiment, a pervaporative sleeve or housing is used to cool a body such as a drinking vessel or container in contact with the sleeve. The resulting liquid vapor is lost to the surrounding environment or to an absorbent material through the matrix. In most containers, natural convection and conductive heat transfer within the liquid are predominant heat transfer mechanisms responsible for cooling the liquid contents of the container. Depending upon the dimensions and other properties of the container, the cooling may be substantially uniform throughout the container.

The liquid contents of the pervaporative container or sleeve acts as a coolant. Preferably the liquid volume loss is marginal; for example, in one embodiment, the liquid volume loss of approximately 15% over a 24 hour time period even with significant external air circulation. Due to the high latent heat of vaporization of water (583 cal/g at 75° F.), for example, approximately seven times as much weight in ice would be required to maintain the same temperature drop as a loss of water due to vaporization. An added benefit of the porous matrix in addition to pervaporative cooling is in venting any pressure differential developed in the container due to the release of carbonation from a beverage or due to the consumption of the contents.

Referring now to the drawings, there is shown in FIGS. 1A and 1B one embodiment of a vented pervaporative cooling container formed in accordance with this invention. The wall 501 of the container is formed at least in part of pervaporative matrix. This vapor permeable matrix can be from about 5 to 100% of the total surface area of the container. Approximately 100% coverage is achieved if the entire cap and housing (comprising the top 500 walls 501 and bottom 502) are made from porous matrix material. In one preferred embodiment, the pervaporative surface area is greater than about 30% of the total container surface and provides a substantial amount of pervaporative flux to effectively cool the contained liquid below ambient temperature and maintain a subambient liquid temperature.

Figure 2:
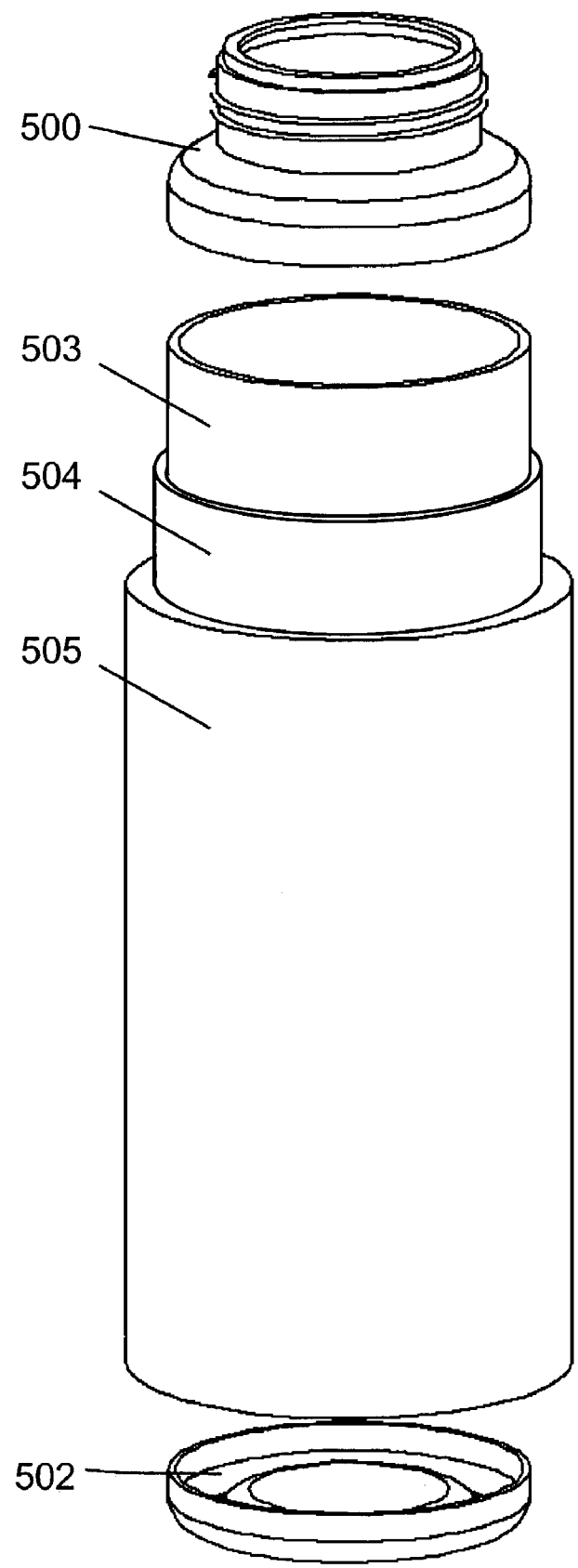
FIG. 2 shows a partially exploded view of a multilayered structure according to one embodiment comprising a thin membrane layered between two macroporous layers

In one embodiment, as shown in FIG. 2, a multilayered construct comprising two or more layers may be used. In one embodiment three layers of porous material 503, 504 and 505 are used to obtain a multilayer or laminate matrix. In one embodiment, a sintered macroporous matrix of polyethylene 505 with a thin layer of expanded PTFE 504 on the liquid side of the container increases the hydrophobicity and liquid intrusion pressure but helps to maintain a similar pervaporative flux and good mechanical stability as is obtained using porous polyethylene by itsel. In addition, a third layer of porous polyethylene 503 forming a sandwich with the expanded PTFE in the middle 504 provides a scratch resistance surface close to the inside of the container making it dishwasher safe and substantially preventing or reducing the soft expanded PTFE layer from being damaged. In related embodiments, laminates can comprise greater or fewer than three layers and/or different porous matrix materials.

In an alternate embodiment, the inner layer 503 comprises a pervaporative matrix or laminated matrix, middle layer 504 comprises a thermally insulative material with pores or other open spaces to allow passage of the vapor, and outer layer 505 comprises a desiccant or absorbent material.

A preferred orientation of the matrix is where a higher liquid intrusion membrane faces the inside of the container and the porous matrix support is exposed to the air outside of the container. Thicknesses for these porous materials in a preferred embodiment are in the range from about $\frac{1}{1000}$" (0.025 mm) to $\frac{1}{4}$" (6.4 mm). The porous matrices can also provide structural rigidity, scratch resistance, and/or mechanical integrity to the walls of the container.

In a preferred embodiment, a membrane or thin layer of material with a small pore size (<10 µm) can be selected from a group of highly hydrophobic materials such as expanded polytetrafluoroethylene (ePTFE) and laminated in between thicker highly porous supports such as sintered polyethylene, which allow for a substantial pervaporative flux. If only two layers are used, Each of these layers can vary in thickness from a monoatomic surface treatment to $\frac{1}{4}$" (6.4 mm) in thickness or greater for a foam insulation or porous composite. Porous ceramic materials including molecular sieves (zeolites) or porous polymer films (CSP Technologies—Auburn, Ala.) and organic matrices such as activated carbon can be used to substantially prevent or reduce odors from the environment from contaminating the liquid contents of the pervaporative cooling device or container.

In a preferred embodiment, a layered construct comprises five layers: an inner ePTFE layer, a porous polypropylene, a thermally insulative urethane foam layer, a ceramic such as zeolite and a thin nonporous polyolefin or polyester outer wrap. This device can be used to maintain a pervaporative cool within the device in a humid environment. Upon absorption of the vapor released from the liquid, the zeolite or other desiccant transfers the heat directly or indirectly into the environment while the insulated liquid contents within the pervaporative sleeve are cooled. The outer two layers comprising zeolite and a nonporous film may be disposable or regenerable such as by drying in an oven.

Except for any surface treatments that may be applied directly to the porous matrices in the constructs, the porosities of the matrices or composite are preferably maintained between about 10 to 95%. This provides for structural support within the matrix and enhances the available pervaporative surface area and hence the overall cooling rate of the container. The pore size of the matrix can also have an effect with Knudsen diffusion predominating below a pore size of 200 nm, effectively decreasing the vapor permeation rate and extending the liquid to vapor transition and cooling zone to the air/vapor surface of the material. In accordance with one embodiment, preferred pore sizes include those between about 0.5 µm to 30 µm, which are larger than the Knudsen diffusion range. The liquid intrusion pressure decreases substantially above a 100 µm pore size, making the use of a single layer of macroporous material less desirable in some instances. If a combination of a membrane and a macroporous support are used, then larger pore sizes in the macroporous support become more desirable than in the absence of the combination.

Figures 3A, 3B:
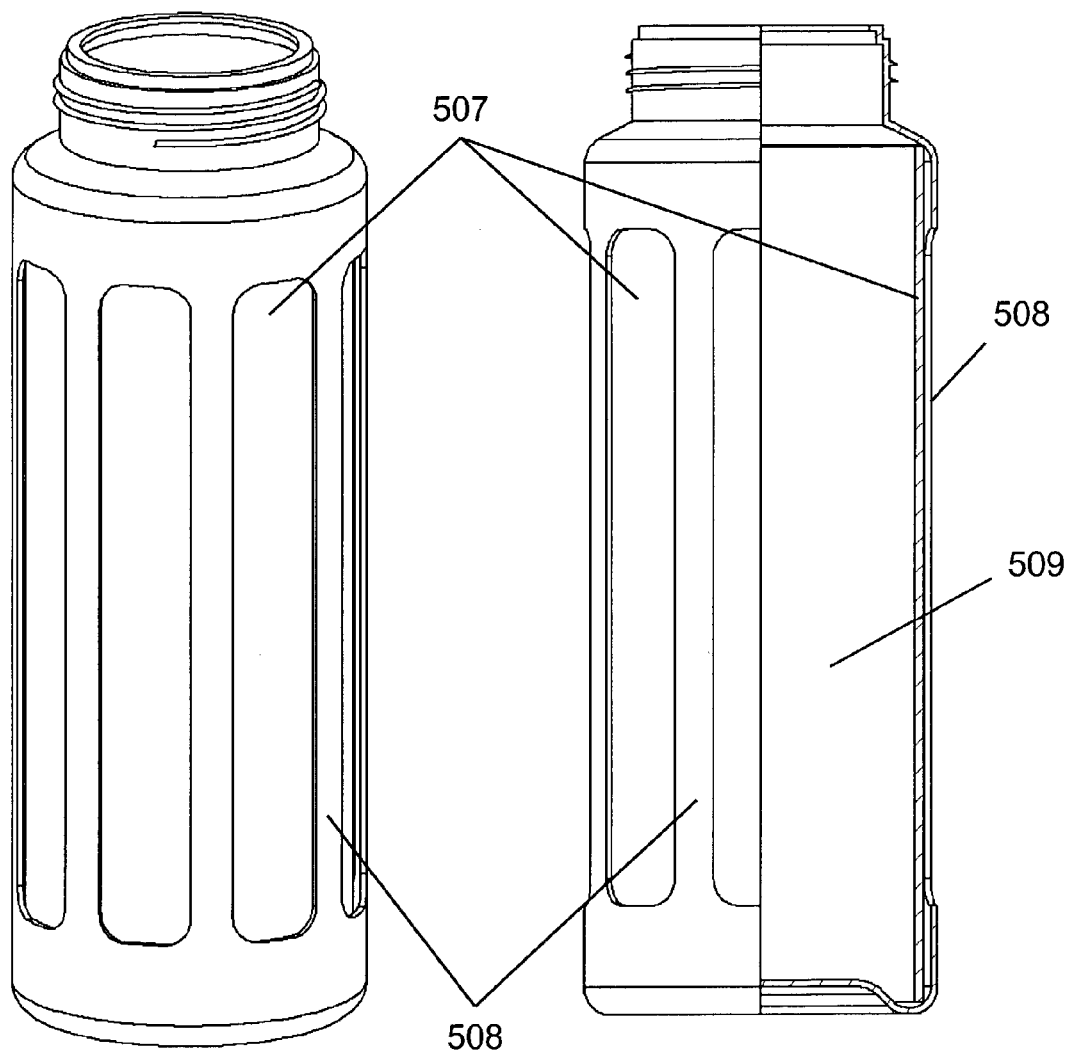

As shown in FIGS. 3A, 3B, 3C, and 3D ribs 508 and 514 may be added to the inside and/or outside walls of the container to enhance the structural rigidity of the container, prevent or reduce damage to the pervaporative matrix 507 and 513 and/or provide a handhold 514. FIGS. 3C and 3F show a sports version of the ribbed design with a narrowed neck 512.

The embodiment in FIG. 4 comprises a layer of open cell porous insulator 518 may be added to the outside surface of the container to allow for relatively unimpeded vapor diffusion out of the system but reduced convective and radiative heat flow from the surrounding environment through the inner container walls 517 and into the liquid. A beneficial feature of this insulator 518 is that it aides as an additional structural support, provides a hand grip on the container and to reduce or prevent damage to the matrix 517. As used herein, "pleated" includes rippled surfaces and other configurations for increasing surface area. Pleated matrices include those in which the entire surface is pleated, or in which one or more portions are pleated and others are left smooth.

Use of a pleated membrane or pleated porous sintered matrix 520, as shown in FIG. 5, can enhance the pervaporative cooling of the container since the rate of pervaporative cooling is a direct function of the surface area of the container.

Pervaporative containers and garments may comprise an adjustable or movable sleeve on the outside of the pervaporative matrix to allow for selective covering or uncovering of some or all of the pervaporative material. Covering some of the pervaporative material reduces the vapor flux rate is while still maintaining some pervaporative cool. Covering all substantially stops the pervaporation and can serve as a type of "on-off" switch for the container or garment.

For example, sleeves 524 and 525, as shown in FIGS. 6A and 6B can be provided as a means to reduce the exposed porous surface area 527 and overall evaporative cooling rate of the container and hence reduce the liquid vaporization rate and cooling rate allowing for greater control of the temperature of the container contents. Reduced cooling may be desired in some situations such as when the absolute pressure, relative humidity and/or ambient temperature are low. As shown in FIG. 6B, there is preferably a separation or gap 530 between one or more portions between the container and the surrounding sleeve. The gap can serve as an insulating region and/or as a region of buoyant natural convective flow of vapor, allowing for the maintenance of pervaporative cooling and the minimization of radiative heat transfer to the liquid contents 529 of the container. The inner sleeve 524 on the outside of the porous matrix 523 of the container is preferably attached to the pervaporative matrix at least at the top 522 and bottom 526 portions of the container housing, especially if such portions are nonporous.

In one embodiment, some or all of a pervaporative garment or container may comprise a pervaporative sponge which both holds water within the body of the sponge and also serves to provide cooling by pervaporation. One preferred embodiment is a two-layer pervaporative sponge having an inner sponge comprising a hydrophilic material and an outer hydrophobic layer attached thereto. In this configuration, the inner sponge can be soaked with water or another vaporizable liquid prior to use and the porous hydrophobic top layer substantially prevents or reduces the leakage of the pervaporative liquid at the outer surface of the pervaporative matrix. The liquid provides a heat transfer path through the wet matrix directly to the inner container wall surface.

FIG. 7 illustrates a two-layer pervaporative sponge 533 that can be used on glasses, bottles and containers. This configuration allows the inner sponge layer 534 to be soaked with water or another vaporizable liquid and a porous hydrophobic top layer 535 substantially prevents or reduces the leakage of the liquid coolant at the outer surface of the pervaporative matrix 535. The liquid provides a heat transfer path through the wet matrix directly to the inner container wall surface 532.

FIG. 8 shows an alternate configuration in which a cooling jacket 542 holding water or another pervaporative fluid 541 is filled through the port 543 and used to cool the contents of an enclosed container housing 539. The housing comprises one or more sections of pervaporative matrix 537 and optionally comprises one or more ribs 538 to enhance structural strength. The liquid contents 540 within the enclosed central housing 539 can thus be sealed, substantially preventing or reducing the loss of liquid volume or carbonation within this region. In addition, the pervaporative cooling efficiency of the container is not dependent on the nature of the enclosed liquid; it depends only on the volatility, heat of vaporization, ionic strength (tonicity) and solute content of the water or liquid 541 used to fill the surrounding housing. As shown in FIG. 7 the cooling jacket may also be made of a detachable sleeve consisting of an outer hydrophobic pervaporative layer 535 and an inner porous liquid holding or absorbing layer 534.

Figure 10:
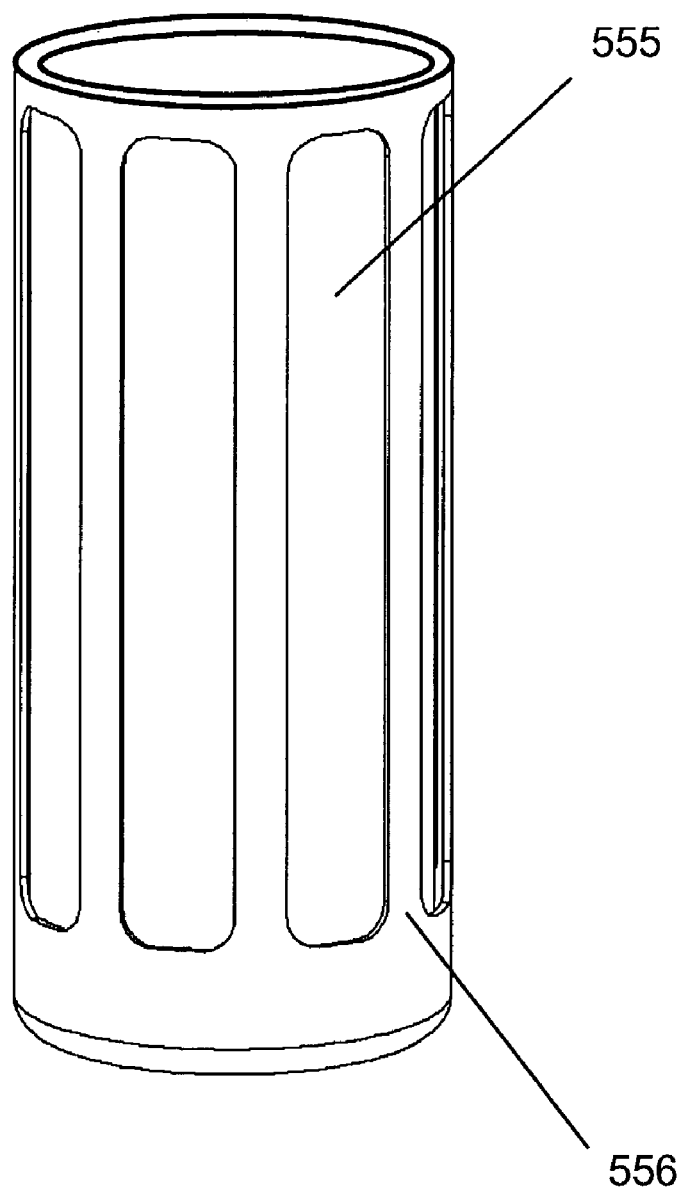
FIG. 10 illustrates one embodiment of a pervaporatively-cooled drinking cup.

FIG. 10 illustrates a pervaporatively-cooled drinking cup similar in function to the pervaporative bottles shown in FIGS. 1A, 1B, 2, 3A and 3B. As soon as liquid is poured into the cup the porous matrix 555 allows the liquid to pervaporatively chill. The bottle housing and support ribs 556 provide structural support and insulation.

These types of cooling jackets 533 and 542 can also be used in a similar configuration as a food cooler to reduce and maintain the temperature of the contents 568 below ambient. In one embodiment, as shown FIGS. 11A, 11B and 11C, baffles 560, 565 and 573 can be used on the cooler to protect the pervaporative matrix 566, and to aide in the mechanical rigidity and handling of the storage container. Both the lid 558, 572 and bottom 563, 559 portions of the cooler can be filled with water or another pervaporative liquid 567 and 575 through the liquid fill and drain ports 561 and 576. The inside of the lid 574 and the bottom 569 portions of the container are preferably made of a nonporous material.

Figure 12:
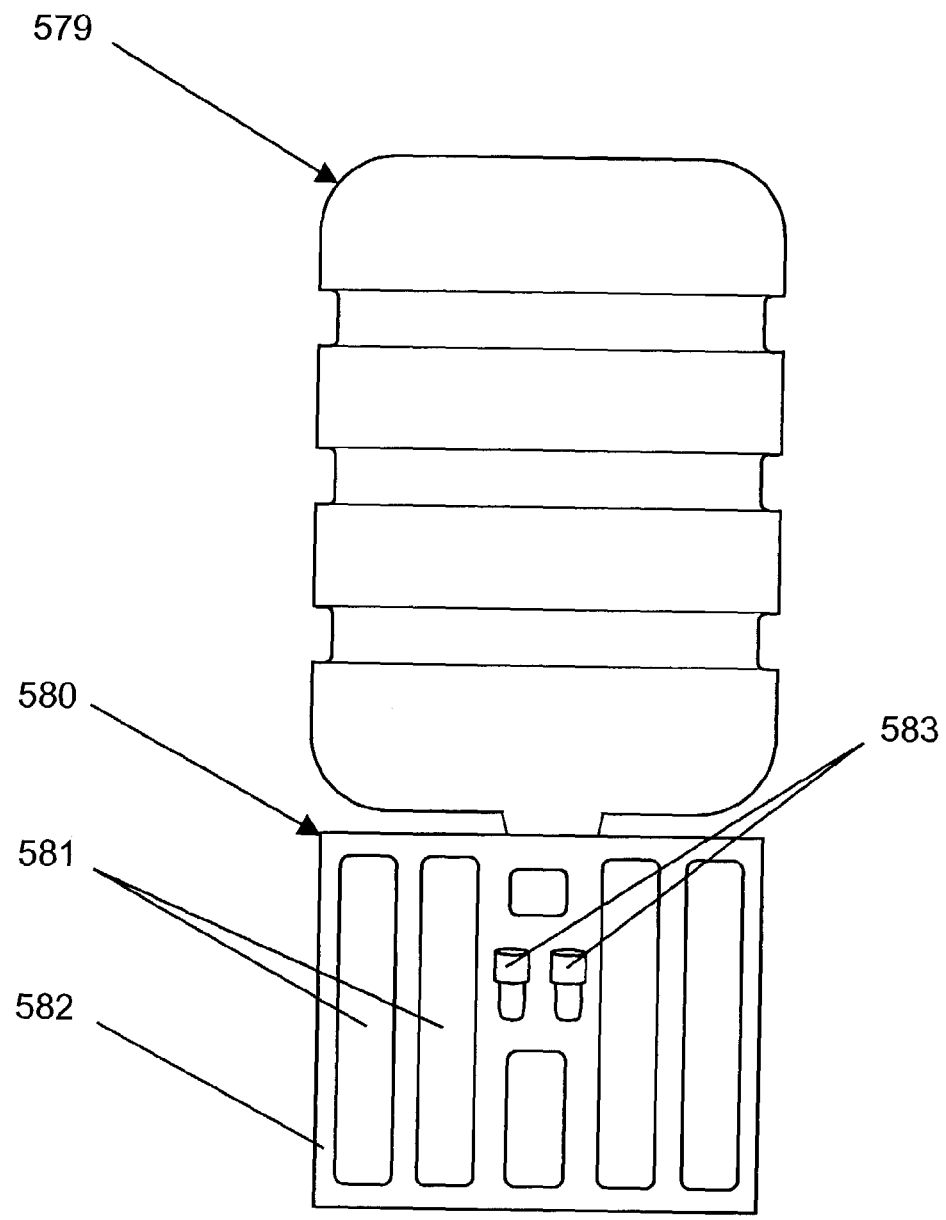
FIG. 12 illustrates a preferred liquid dispensing reservoir comprising a pervaporative matrix.

FIG. 12 illustrates a chilled water dispenser comprising of a high capacity water bottle 579, such as a 5 or 10 gallon bottle, and a pervaporatively chilled liquid dispensing reservoir 580. As the liquid is replenished in the reservoir 580 from the bottle 579, the pervaporative matrix 581 surrounding the reservoir chills the liquid prior to being dispensed from one or more port valves 583. Alternately, one valve can be used for chilled water and one valve can be used for hot water. Pervaporative cooling reduces or eliminates the need for an electrical chilling mechanism such as a refrigerant compressor. The plastic housing 582 of the reservoir 580 provides mechanical support for the pervaporative matrix 581.

Figure 13:
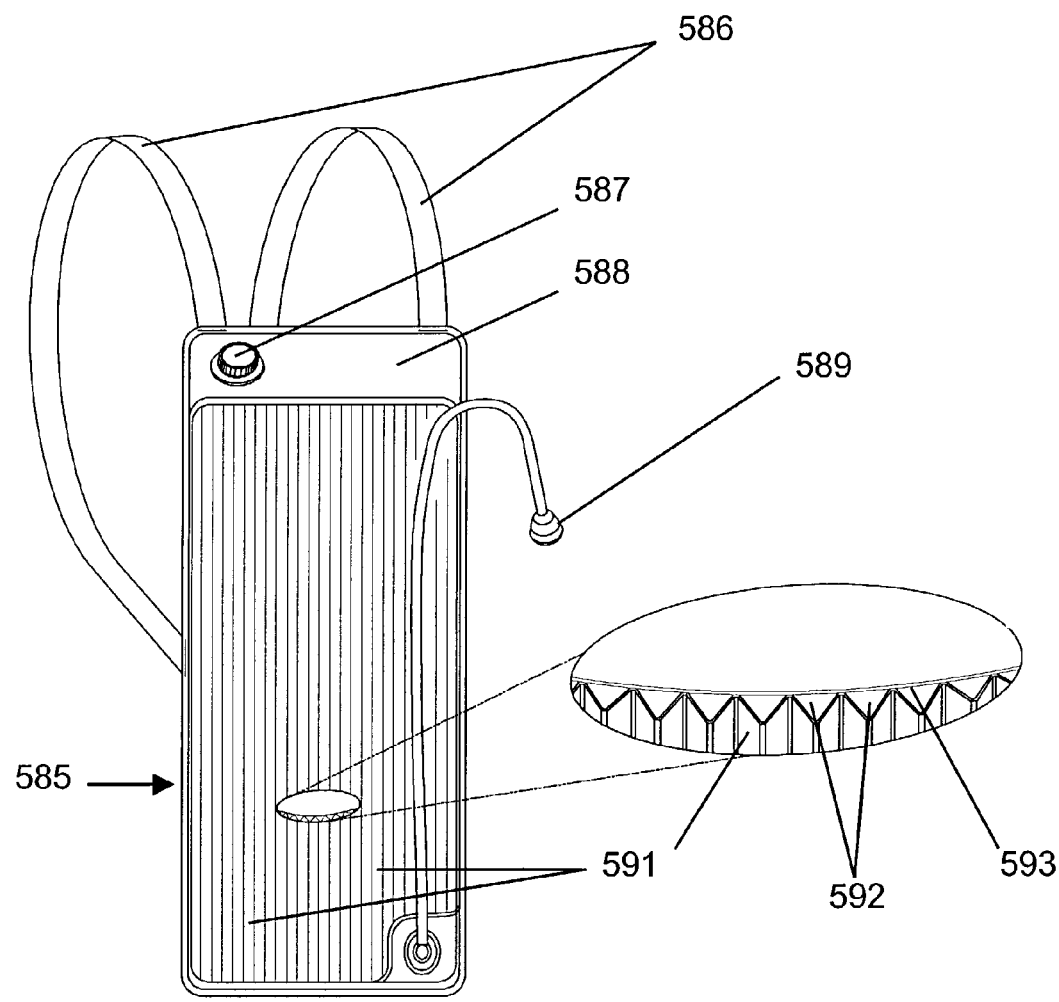
FIG. 13 illustrates one embodiment of a hydration backpack comprising a pleated pervaporatively-cooled reservoir filled with liquid.

In one embodiment, a pervaporative container may comprise one or more straps so as to allow the container to be carried on the body. The container may be worn in any manner, including but not limited to, being strapped around the torso or a limb or worn in the form of a backpack or purse. Potential market applications of this technology fit within the scope of pervaporatively cooled sports equipment to optimize athlete performance. FIG. 13 shows one embodiment of a pervaporatively cooled hydration pack 585. The pack comprises a body 588 comprising pervaporative matrix 591, which in one embodiment is ribbed to provide greater pervaporative surface area. The pack is filled with pervaporative fluid through the fill drain port 587 and can be carried by means of one or more straps 586. A drinking tube 589 is in fluid communication with the interior of the pack is preferably included to allow the carrier to conveniently drink the fluid. Pervaporatively-cooled hydration pack, including backpack-type wearable/carryable containers may be constructed by forming at least a portion of the bladder component of any of a variety of hydration packs as are known in the art and are available commercially (e.g.

CamelBak, Petaluma, Calif.; HydraPak, Berkeley, Calif.) with a pervaporative material such as by heat sealing, adhesive and/or stitching techniques.

In one embodiment, a hydration pack 585 comprises a laminate of at least two layers: (1) an outer layer 591 comprising a pleated or nonpleated pervaporative layer comprising a hydrophobic pervaporative laminate; (2) a support layer 593 including a, preferably, thin support layer for the pervaporative layer 591 which acts as a liquid barrier. In some embodiments, such as for extended operations, water is fed by gravity or by wicking from a liquid holding reservoir 588 down into the interstices 592 formed between the pervaporative matrix 591 and the middle layer 593.

An optional third layer preferably comprises insulation and directly touches the skin (or is in thermal contact with the skin through clothing) and provides a thermal barrier between the user and the hydration pack. This layer may be continuous or have a bumped pattern (e.g. fluted, pleated, scalloped) to allow the passage of air between the user and the hydration pack. An optional third or fourth layer comprises a desiccant or absorbent material.

Figure 14:
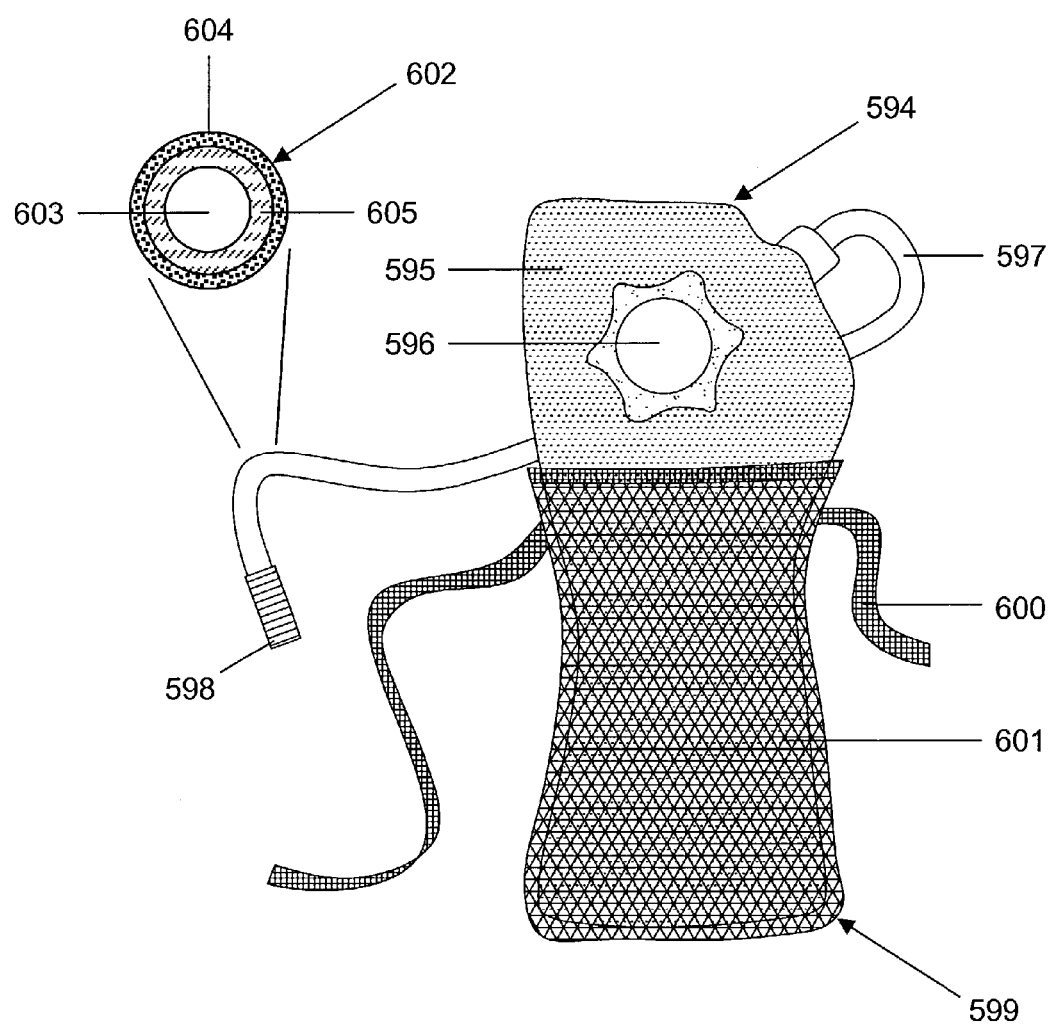
FIG. 14 illustrates a pervaporatively-cooled drinking pouch in an optional porous webbed strap on holder. In addition an internally wettable pervaporatively-cooled tube is shown, which can be used for immediately-chilled drinking or dispensing in connection with the illustrated pouch or with other containers.

FIG. 14 shows a pervaporatively-cooled drinking pouch 594 in an optional webbed strap-on holder 599. The holder may comprise materials other than webbing; it need only be able to hold the pouch and preferably not substantially interfere with pervaporation. A pervaporative pouch such as this can, for example, be strapped into a belt loop using securing straps 600 or attached to the side of an existing belt. The webbing 601 allows a free path for the porous pouch matrix 595 to pervaporate. The pouch 594, in one preferred embodiment, comprises three main parts: 1) the pervaporative body 595 comprising a pervaporative matrix, 2) a fill port 596 and 3) a pervaporatively chilled drinking tube 597, 602 and a valved spout 598. The body 595 may be made substantially entirely or in part of pervaporative matrix. The pervaporatively cooled drinking tube 602, in one embodiment, comprises an outer pervaporative hydrophobic layer 604, which substantially prevents or reduces liquid leakage and pervaporative cooling, and an internal liquid wettable layer 605. Once liquid is introduced through the center 603 of this layered construct 602 the liquid penetrates into the hydrophilic material producing a liquid lock 605 which substantially substantially prevents or reduces air form entering the center of the tube 603 through the porous matrix 604. The liquid trapped in the hydrophilic matrix 605 is free to pervaporate through the outer hydrophobic matrix 604. This combination of hydrophilic 605 and hydrophobic 604 matrices in a tube format 602 provides the benefit of delivering chilled drinking water directly from the internal tube volume 603 when placed in combination with a pervaporatively cooled reservoir 594 or with a non-pervaporatively cooled reservoir, in an alternate embodiment. One simple method of manufacture of such a device 602 is to plasma treat the center of a hydrophobic porous PTFE tube. Alternatively, the drinking tube may be made of non-pervaporative materials.

In some embodiments, the pervaporative container is in the form of a lightweight liquid-filled (preferably water-filled) pervaporative cooling garment that serves as a simple personal microclimate cooling system to relieve heat stress in individuals wearing protective clothing, in normal or elevated ambient temperature conditions. This type of cooling garment can be manufactured into protective suits, such as chemically or biologically protective suits or Nomex fire suits, to form a part of such clothing or it may be worn in conjunction with such protective garments. Alternatively, the garment can be worn under a layer of body armor.

A cooling garment according to preferred embodiments, can be used for many purposes, including, but not limited to, fire and rescue personnel, military personnel, and hazardous (chemical and/or biological) materials workers, as well as for sports enthusiasts who could increase their endurance by releasing more heat from their bodies during sporting activities. Pervaporative garments can also lower the amount of infrared radiation given off by the wearer. In preferred embodiments, water or a combination of water and ethanol (preferably about 5 to 15%) as a pervaporative coolant source is used to allow the device to be substantially non-hazardous and provide an additional functionality such as an extra pouch for pervaporatively-chilled drinking water for the wearer. Chilled drinking water can also lessen the heat load on an individual wearing a protective suit or clothing or engaging in sporting activities, especially those requiring endurance. Although non-hazardous and/or potable coolants are preferred, any liquid capable of providing pervaporative cooling functionality may be utilized, including methanol, isopropanol, non-potable water, and other liquids and solvents. Preferably, the coolant chosen is compatible with the material(s) it contacts within the garment.

In one preferred embodiment, a pervaporative cooling garment is in the form of a jacket or vest. The pervaporative garment may be worn alone or it may be worn incorporated or integrated into another article of clothing or garment, such as a protective suit. When incorporated or integrated into another garment, the pervaporative garment preferably comprises the innermost layers so as to be in close contact (i.e. in thermal contact) with the wearer. The pervaporative cooling garment may be in direct contact with the skin or it may be in contact with other clothing worn by the wearer. In some embodiments, the pervaporative garment comprises a layer of fabric or material covering some or all of the portion of the pervaporative matrix which is directed toward the inner portion of the garment (i.e. the portion that touches or is in thermal contact with the wearer).

Although the discussion regarding pervaporative garments is in terms of a vest or jacket having a particular configuration, this discussion should not be construed to limit the disclosed invention. The principles discussed herein provide for a variety of pervaporatively cooled garments, including jackets, hats, belts, pants, leggings, and structures that encase one or more parts of the body, such as a wrap for a leg or arm (or a portion thereof), or the neck.

Figure 15:
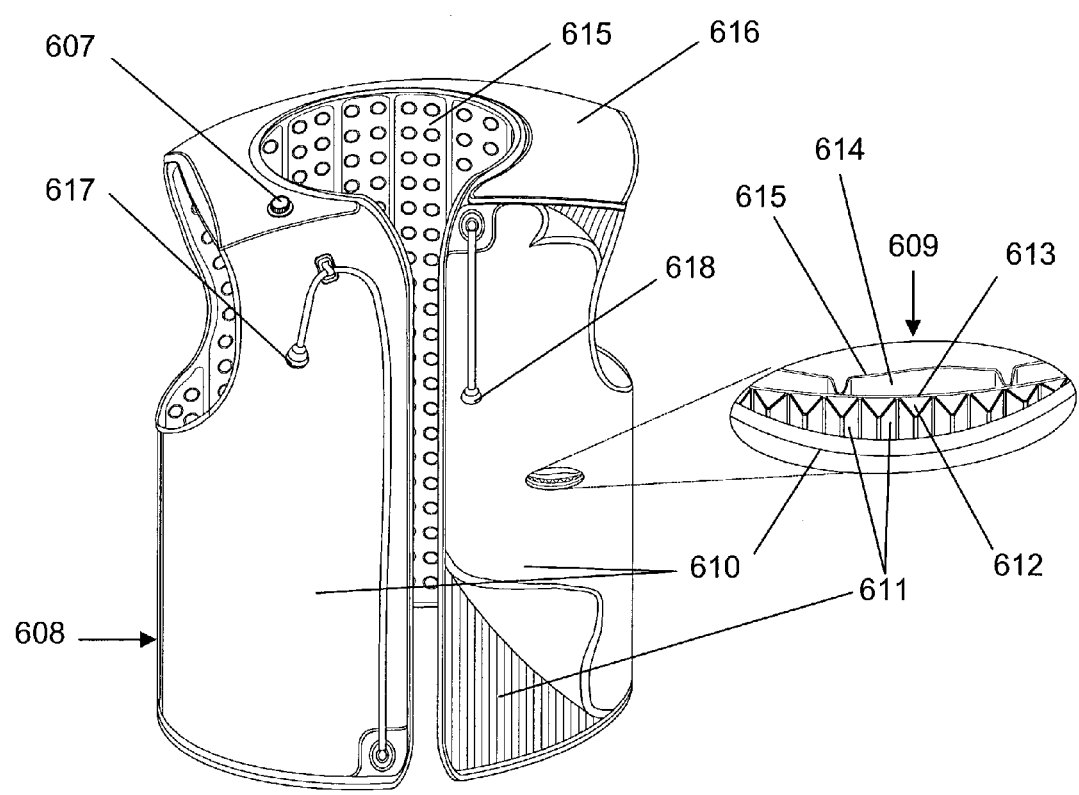
FIG. 15 illustrates a pervaporatively cooled jacket according to one embodiment.

FIG. 15 shows a design of one preferred embodiment of a jacket 608. The jacket may be worn alone or the jacket or vest may be hidden under clothing or protective clothing such as a chemical suit, Nomex fire suit or body armor.

In a preferred embodiment, the jacket comprises a laminate of three or four layers:

(1) an optional regenerable or disposable outer layer 610 comprising a desiccant or an absorbent material that absorbs the moisture or other fluid resulting from pervaporation (2) an outer layer comprising a pervaporative layer 611, preferably pleated, comprising a pervaporative laminate, preferably hydrophobic in nature;

(3) a middle layer 613 comprising a thin support layer for the pervaporative layer that may also act as a liquid barrier, and in some embodiments, a barrier to potentially hazardous biological or chemical materials. For extended operations, in one embodiment, water or other cooling fluid can be fed by gravity or by wicking from a liquid holding reservoir 616 such as on the shoulders of the jacket down into the interstices 612 formed between the pervaporative matrix and the middle layer; and (4) an inner layer 615 that is in contact with the skin, directly or through a piece of fabric or material, such fabric or material being part of the jacket itself and/or a separate item worn by the wearer. The inner layer preferably comprises patterned or serpentine regions formed by a heat sealing process. In one embodiment, there is provided a simplified jacket comprising only layers 2 and 4 above.

The fluid may be placed in the jacket through the port 607 on the jacket. In a preferred embodiment, the space 614 between the inner and middle layers forms an air bladder which, when inflated via a mouthpiece 618, provides insulation from the liquid in the cooling jacket. When the air bladder is collapsed via the terminal mouth piece on the air hose, the liquid layer comes into thermal contact with the skin through the stacking of the middle and inner layers and this provides on demand cooling. In another embodiment, a segregated water reservoir in the jacket is sandwiched between the middle and an inner insulative layers to provide a cool source of drinking water. Optionally, the reservoir may comprise a collapsible bag to prevent water from sloshing around which may create undue or undesirable noise. In other embodiments, the garment may comprise a drinking tube 617 to allow the wearer to consume the liquid in the jacket.

If a pervaporative garment not having an outer desiccant/absorbent layer is worn under clothing, protective or otherwise, it is preferred that such clothing be permeable to the pervaporative fluid or that the clothing have vents, pores or other openings to allow for passage of the pervaporative fluid.

In some embodiments, the pervaporative garment further comprises a regenerable or disposable outer layer comprising a desiccant or an absorbent material that absorbs the moisture or other fluid resulting from pervaporation. Suitable desiccants or absorbent materials for aqueous pervaporative fluid include, but are not limited to, ammonium sulfate, molecular sieves and polyacrylic acid. The outer desiccant/absorbent layer can be discarded following use or it may be regenerated such as by application of heat and/or reduced pressure. In a preferred embodiment, the absorbent/desiccant layer absorbs at least about 3–4 times its weight in water. The process of absorbing water in the layer is preferably endothermic or at least minimally exothermic. In preferred embodiments, this layer provides a high degree of absorbancy, dimensional stability and/or minimizes heating due to water vapor hydration in this layer. As will be readily understood by those skilled in the art, a desiccant or absorbent layer may be used in combination with any pervaporative container described herein. When a pervaporative garment of this type is used in combination with or incorporated or integrated into another garment, there is no need for pores, vents, openings and the like in the other garment, although they may be present if desired. In a related embodiment, at least one surface of the outer desiccant/absorbant layer comprises a material which is chemically resistant and/or substantially impervious to chemical and/or biological agents to provide additional protection to the wearer.

The following is brief look at the thermodynamic feasibility of such a construction. Assuming an average water vapor pervaporative flux through a porous matrix of $4*10-6$ $g*cm-2*s-1$ at 75° F. in still air from Table 1 and assuming the water vapor flux is doubled at 95° F. gives $8*10-6$ $g*cm-2*s-1$ as the flux. If the enthalpy of vaporization at 95° F. is 2400 J/g, then the energy dissipation per unit area of the matrix is $1.9*10-2$ $Watts*cm-2$. In order to achieve a power dissipation of 25 Watts approximately 1500 cm2 or 1.5 ft2 of available matrix surface area needs to be used in the construction the hydration pack. Use of a pleated membrane or a pleated porous sintered matrix to enhance the pervaporative cooling power, since pervaporative cooling power is a direct function of the porous surface area of the jacket. In order to cool for 4 hours at this rate approximately 150 mL of water will be spent in the process. Thereby a little under 0.5 lbs. of water will be used in the process. It would seem reasonable that a water filled jacket like this may be made to weigh approximately 3 lbs or less.

As will be understood by those skilled in the art, the various layer configurations in the embodiments of jacket, pouch, and backpack discussed above are interchangeable, as they are interchangeable with other container configurations disclosed herein.

A preferred orientation of multilayer or multifunctional matrix according to one embodiment is where the higher liquid intrusion matrix surface faces the inside of the garment and the matrix supporting backing is exposed to the air outside of the garment. Thicknesses for these porous materials in a preferred embodiment are in the range from about 1/128" (0.2 mm) to 1/8" (3.2 mm). In one embodiment, layered composites of membranes and pervaporative matrices are selected to provide both a high liquid intrusion pressure at the liquid/matrix interface using a thin highly hydrophobic material with a small pore size such as expanded polytetrafluoroethylene (ePTFE) laminated in between thicker highly porous supports such as sintered polyethylene, which allow for a substantial pervaporative flux.

Methods of Manufacture

Several processes are available for the manufacture of pervaporative containers or the pervaporative matrix portion of a pervaporative garment including, but not limited to, sintering sub-millimeter size plastic beads in a mold cavity to directly form the pervaporation wall; thermal or ultrasonic lamination or welding of one or more pieces of pervaporative matrix together or to a suitable frame; insert molding whereby one or more sheets or a cylinder of the porous matrix is inserted into the cavity of a mold and a thermoplastic polymer is injection molded directly around the insert(s) to form the desired composite having porous matrix portions; heat sealing; attaching components using adhesives; and/or stitching techniques may also be used to assemble all or part of a pervaporative garment or container.

Multilayered constructs containing two or more layers of porous material may be used to obtain a mechanical and physically superior matrix. For instance, combining a sintered macroporous matrix of polyethylene with a thin layer of expanded PTFE on the liquid side of a container increases the hydrophobicity and liquid breakthrough pressure of water from 5 psi to over 30 psi, yet the layered matrix still maintains a similar pervaporative flux to that obtained using porous polyethylene by itself.

FIGS. 1A and 25B show the construction of a preferred embodiment of a pervaporative container with a wall portion 501 comprising pervaporative matrix. The wall 501 is fixed to the top 500 and bottom 502 portions of the container by a process such as by insert molding, thermal or ultrasonic welding, adhesive joining, or other suitable means. Insert injection molding may also be used to attach the matrix to the other portions of the container. The top of the bottle 500 illustrated in this example allows for a threaded fit and can be used with a vented bottle cap. The top 500 and bottom 502 portions of the container may be made by any suitable method, including injection molding, vacuum forming, and the like.

FIGS. 3A and 3B show a ribbed configuration for a thin pervaporative matrix 507 for which additional structural support 508 is desired. The ribs 508 give the container wall both structural integrity and a ridged surface for a firmer hand grasp on the container. The ribs 508 can be placed on the outside, inside and/or one or more sides of the pervaporative matrix. The ribs 508 are preferably injection molded by insert molding onto the pervaporative matrix 507. Alternatively, ribs 508 can be sealed to a porous matrix 507 or porous matrix 507 can be sealed to a ribbed container shell 508 by ultrasonic, thermal or adhesive means, among others.

FIGS. 3C and 3D demonstrate a sports version of this container which allows the container to be fixed securely in a holding bracket by the bottle neck 512. The mouth of the bottle 511 allows for the use of various closures, including a snap lid and threaded closure.

FIG. 4 shows a thermally insulating, hydrophobic open cell foam layer 518 that allows water vapor to move through the open cell structure, but impedes the convective and radiative heating of the container contents. Table 1 demonstrates that the thermally insulating matrix reduces the liquid loss rate while maintaining a substantial pervaporative cool. In a preferred embodiment, the insulating foam 518 is placed or taken off of the bottle as an elastic sleeve.

Increases in pervaporative cooling efficiency can be achieved by increasing the surface area of the matrix in contact with the liquid by pleating the matrix. FIG. 5 shows a pleated container body 520 that allows for a greater pervaporative surface area to be exposed per contained liquid volume. This configuration allows for a decrease in the time taken to pervaporatively cool the container volume. A container having this configuration can be made by insert molding or by potting both ends with adhesive to a bottom 521 and top 519 container elements or with molten plastic.

FIGS. 6A and 6B demonstrate a rotating sleeve 525 on the outside of the matrix body 523. As the outer sleeve 525 rotates past the inner sleeve 524, a set of vertical slits 527 is formed, which open and close to allow variable exposure to the pervaporative matrix 523, thereby reducing the vapor flux rate but still maintaining an adequate pervaporative cool. A vertical slip sleeve, whose slits are adjusted vertically instead of by rotation, may also be used in a configuration of this type. The inner and outer sleeves 524 and 525 are made of a substantially nonporous material such as plastic or metal that does not allow water vapor to pass. FIG. 6B illustrates the annular sleeve which helps to maintain a very thin gap 530 between the porous matrix 523 and the inner stationary sleeve 524. This gap 530 is useful as a shield to substantially prevent or reduce direct conductive and radiative heat transfer to the porous matrix 523 of the main container body. In addition, this spacing 530 allows for vapor flux out of this annular region 527. The sleeves 524 and 525 may also be used over a pleated pervaporative surface 520 such as shown in FIG. 5. Again, the sleeves 524 and 525 can be placed on the outside of the container by sliding them onto the outside of the container. The inner sleeve 524 may be attached or sealed in place.

FIGS. 7 and 8 show a jacketed embodiments of pervaporative containers. As shown in FIG. 7 the cooling jacket may be made of a detachable sleeve consisting of an outer hydrophobic pervaporative layer 535 and an inner porous liquid holding or absorbing layer 534. In the embodiment of FIG. 8, the outside jacket 541 is filled through special ports 543 with water or other volatile fluids 541 and the contents of the inner liquid container 540 are maintained at a sub-ambient temperature. One advantage to this configuration lies in that a carbonated beverage can be stored in this container without losing carbonation. In addition, a liquid with a low propensity to pervaporate, such as a liquid high in electrolytes or sugar can be placed in the inner chamber 540 of the container while distilled water or other easily pervaporated liquid 541 is placed in the outside chamber to obtain an adequate temperature drop.

Another embodiment for a sponge 533 or jacketed 542 pervaporative configuration as shown in FIGS. 7 and 8 is for the use of an oleophobic pervaporative matrix which retains organic liquids such as alcohol. In such a configuration the outside jacket 533, 542 are be filled with ethanol, and serves as the pervaporative coolant 534, 541.

FIG. 10 illustrates a pervaporatively-cooled drinking cup similar in function to FIGS. 1A, 1B, 2, 3A and 3B. Assembly may be performed wrapping a planar pervaporative matrix around or pushing the matrix 555 over the cup body 556 as a cylinder and attaching the material by adhesive, potting, thermal welding or ultrasonic welding. Insert molding may be used to directly attach the material into the bottle frame and walls.

Figure 11A:
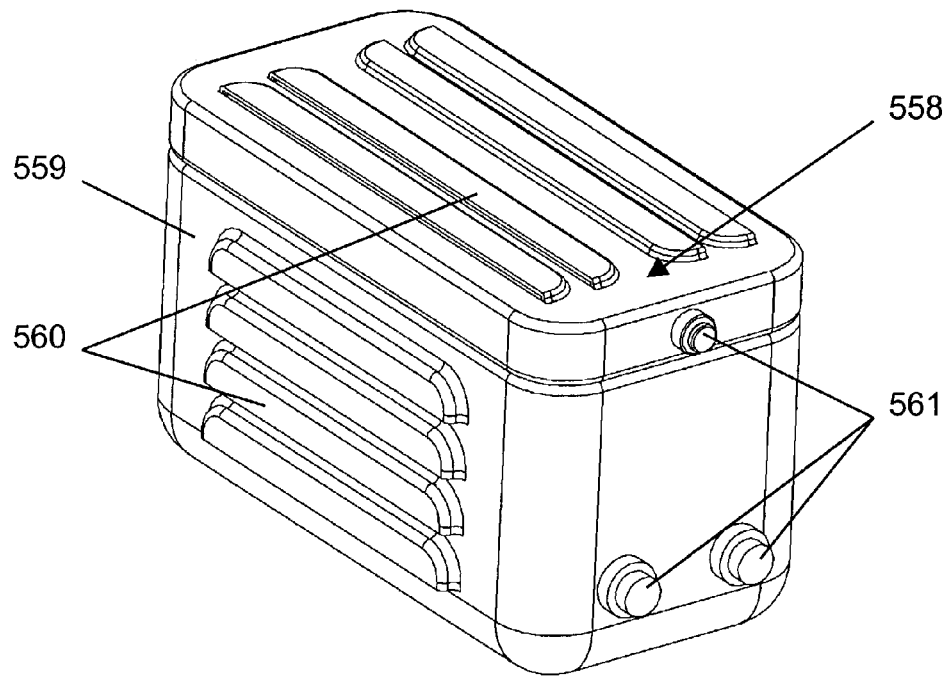
FIGS. 11A, 11B and 11C illustrate one embodiment of pervaporative cooling storage container (e.g. a cooler) having a pervaporative body shell and pervaporative lid.
Figure 11B:
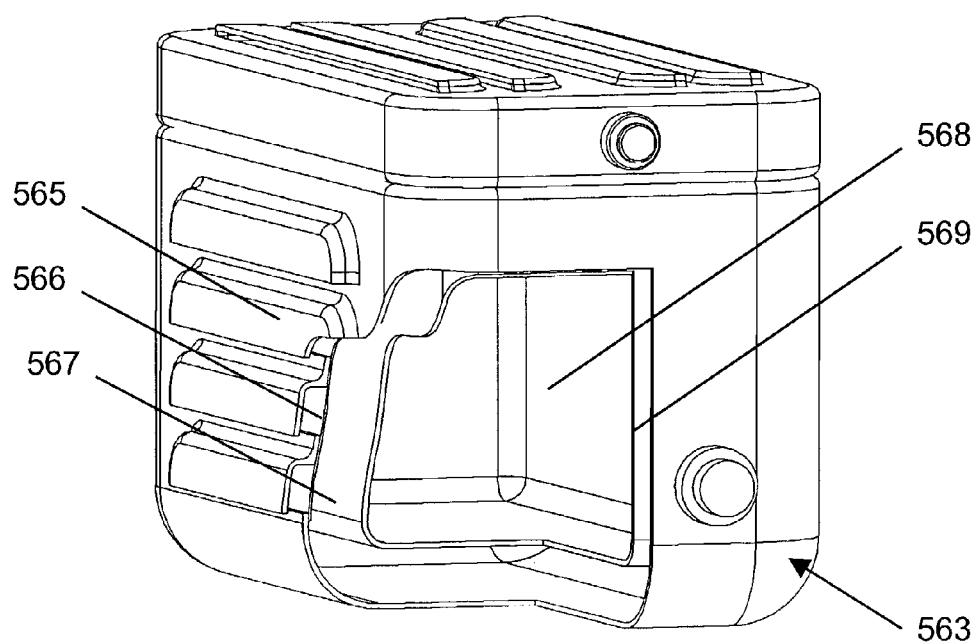
Figure 11C:
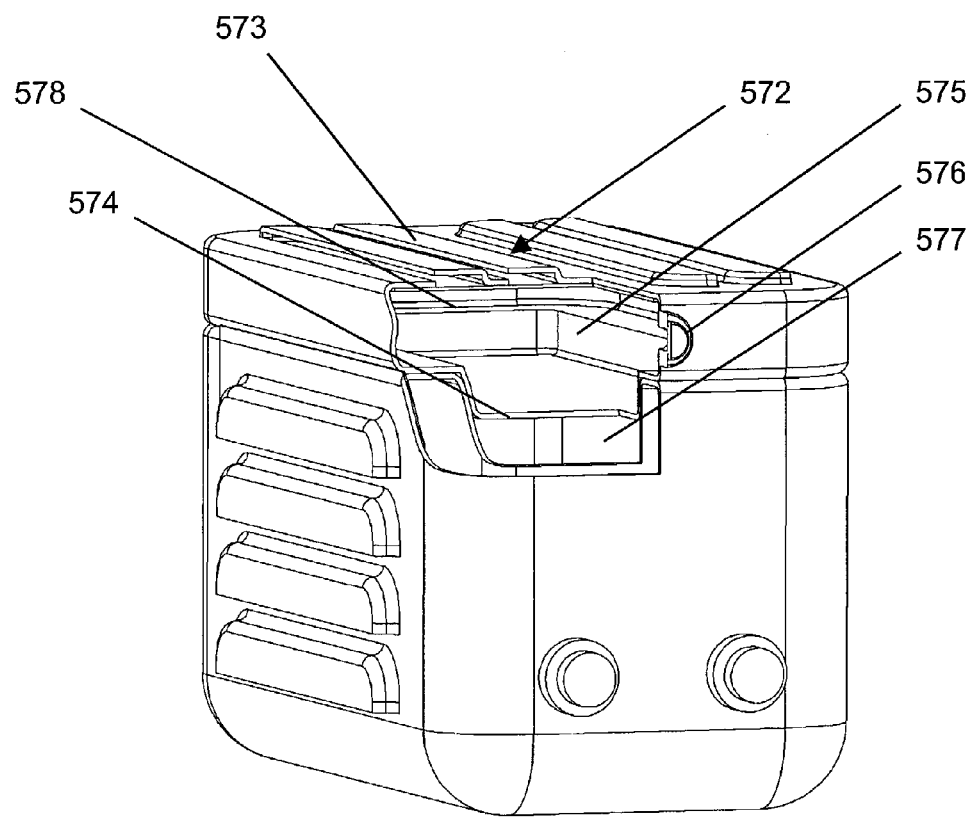

FIGS. 11A, 11B and 11C show a configuration for producing a cooling container for the storage of beverages and foodstuffs 568. In this configuration the lid 558, the cooler walls 559 and 564 or preferably both the lid 572 and the walls 559 and 564 contain a liquid-filled pervaporative jacket 566 and 578. The container may further comprise one or more layers of insulation. The container can be used to store foods and beverages 568 at sub-ambient temperatures for several days at a time. In one embodiment, assembly of the cooler body 563 is performed by placing the planar pervaporative matrix 566 inside the case body 564 and attaching the material by adhesive, potting, thermal welding or ultrasonic welding. Alternatively, insert molding is used to directly attach the material 566 into the frame and walls 564.

One proposed solution for heat stress relief is based on the idea of pervaporation. A chilled hydration pack or other cooling garment utilizing a pervaporative cooling mechanism, such as this would find applications not only in the military as a personal cooling system but also for a sports enthusiast who could increase their endurance by releasing more heat from their bodies during a race. Using water or a combination of water and ethanol (preferably about 5 to 15%) as a pervaporative coolant source allows such a device to be non-hazardous and provide an additional functionality such as an extra pouch for pervaporatively-chilled drinking water. Chilled drinking water would also lessen the heat load on an individual wearing a protective suit or clothing.

The pervaporative hydration pack described herein will follow a design similar to the pervaporative beverage cooling bottles, which were previously designed. A comparison of the cooling efficiency using pervaporative cooling (2400 J/g) versus the heat of fusion (335 J/g) plus the warming of the liquid (105 J/g) to room temperature (77° F.) reveals that pervaporative cooling is five times more efficient on a mass basis than using ice. Tables 1, 2, and 3 provide data to show what happens to the pervaporative cooling bottles under different conditions of wind speed and matrix composition at room temperature and a relative humidity of 30 to 40%.

FIG. 14 shows one embodiment of a pervaporatively-cooled drinking pouch 594, shown in an optional webbed strap-on holder 599. In one embodiment, a strap is attached directly to the body 595 and no holder, webbed or otherwise, is used. A pervaporative pouch such as this can be worn over the shoulder, strapped into a belt loop or another portion of the body using securing straps 600 or similar attachment devices or attached to the side of an existing belt. In one embodiment, the webbing 601 is sewn from nylon netting and the straps 600 are Velcro, a Nylon/Velcro Composite, or other natural or synthetic material. The various portions of the pouch porous matrix 595 can be assembled by thermal sealing, thermal welding, ultrasonic welding or adhesive lamination, or other methods discussed herein in relation to other containers. In one embodiment, a pervaporatively cooled drinking tube 602 comprises an outer pervaporative hydrophobic layer 604, which substantially substantially prevents or reduces liquid leakage and pervaporative cooling, and an internal liquid wettable layer 605. Once liquid is introduced through the center 603 of this layered construct 602 the liquid penetrates into the hydrophilic material producing a liquid lock 605 which prevents or substantially reduces the amount of air entering the center of the tube 603 through the porous matrix 604. The liquid trapped in the hydrophilic matrix 605 is free to pervaporate through the outer hydrophobic matrix 604. This combination of hydrophilic 605 and hydrophobic 604 matrices in a tube format 602 provides the benefit of delivering chilled drinking water directly from the internal tube volume 603. As noted above, this tube may be used with a pervaporative or non-pervaporative pouch, or it may be used with other containers, both pervaporative and non-pervaporative. One method of manufacture of a pervaporative tube 602 is to plasma treat the center of a hydrophobic porous PTFE tube rendering the inner portion of the tube 605 hydrophilic.

Operation of a Pervaporatively Cooled Device

Preferred designs for pervaporative cooling devices are simple and can be operated under ambient conditions to cool and/or maintain the coolness of fluid or solid contents of the container without the weight and portability limitations associated with mechanical pumping or the need for the application of an external mechanical vacuum to increase the pervaporative cooling rate. In a preferred embodiment, the radial dimensions of a container of the type in FIG. 1A are large enough such that convective mixing by natural convection of liquid contents is obtained. This is because, in some cases, the thermal conductivity of the liquid alone may not be high enough to effectively maintain a generally uniform temperature distribution throughout the container. When the liquid at the inner walls of the container are cooled, this reduces the density of the liquid at the inner walls as compared to that in the center. Because of this density difference, the cooler liquid flows down the inside walls of the container to the bottom of the container where it is entrained back up into a circulatory pattern within the middle of the container in a process called natural convection, as opposed to forced convection. When the cooling rate is high enough, convective eddies break off from the side of the container and enhance the mixing rate.

These phenomena and their occurrence can be predicted using a combination of calculated dimensionless parameters, namely the Grashof Number (parameter for fluid buoyancy in a gravitational field) and the Prandlt Number (parameter that describes the thermal and capacitive nature of the liquid). The combination of these two parameters leads to the calculation of the Nusslet Number (an overall heat transfer parameter). Natural convection within a pervaporative container will enhance the cooling efficiency and the cooling rate of the device by allowing for convective heat transfer through the buoyant fluid in lieu of thermal conduction through the same liquid medium.

Table 1 presents endpoint pervaporative cooling data at a relative air humidity of 30% to 41% and different ambient air velocities and the effect of a porous insulative matrix. Tables 2 and 3 present endpoint water pervaporative cooling data at different relative humidities and in the shade (Table 2) or in the presence of direct solar irradiation (Table 3). The pervaporative materials are PTFE (polytetrafluoroethylene) or sintered UHMWPE (ultra high molecular weight polyethylene). X-7744, X-6919, and 402HP are all UHMWPE materials of various porosity, pore size and thickness as outlined in the tables.

TABLE 1

| Matrix Material | Porosity | Pore size (um) | Thickness (mm) | Liquid Loss (%/hr) | Flux (g cm$^2$/s) × 10$^6$ | Cool (° F.) | Cool at 2 mph (° F.) | Cool at 5 mph (° F.) |
|---|---|---|---|---|---|---|---|---|
| Control 1 (PE) | None | None | 1.5 | 0.0 | 0.0 | 0.0 | 0.0 | 0.0 |
| Control 2 (PE) | None | None | 1.5 | 0.0 | 0.0 | 0.0 | 0.0 | 0.0 |
| PVDF | 75% | 0.5 | 0.1 | 0.4–3.0 | 1.9–7.6 | 12.7 | 14.3 | 14.8 |
| UHMWPE | 35–50% | 7 | 0.6 | 0.3–1.0 | 1.2–6.6 | 10.6 | 12.6 | 13.0 |
| PVDF w/foam insulation | 75% | 13.5 | 5.1 | 0.4–1.9 | 2.0–6.5 | 12.1 | 11.5 | 10.7 |
| UHMWPE w/foam insulation | 35–50% | 20 | 5.6 | 0.3–0.8 | 2.2–5.2 | 9.8 | 10.5 | 11.2 |

TABLE 2

Shade/RH 38.6%/75° F.

| Matrix Material | Porosity | Pore Size (μm) | Thickness (mm) | Temperature (° F.) | Pervaporative Cool (° F.) |
|---|---|---|---|---|---|
| Control #1 (PE) | None | None | 1.5 | 72.2 | — |
| Control #2 (PE) | None | None | 1.5 | 71.9 | — |
| X-7744 | 35 to 50% | 7 | 0.6 | 63.6 | 8.4 |
| X-6919 | 35 to 50% | <15 | 1.6 | 65.1 | 6.9 |

TABLE 2-continued

Shade/RH 38.6%/75° F.

| Matrix Material | Porosity | Pore Size (μm) | Thickness (mm) | Temperature (° F.) | Pervaporative Cool (° F.) |
|---|---|---|---|---|---|
| 402HP | 40 to 45% | 40 | 0.6 | 63.4 | 8.7 |
| 402HP | 40 to 45% | 40 | 1.3 | 64.7 | 7.3 |
| Supported PTFE | 75% | >50 | 0.3 | 63.4 | 8.7 |

TABLE 3

Full Sun/RH 41.0%/77° F. (Shaded Sensor)

| Matrix Material | Porosity | Pore Size (μm) | Thickness (mm) | Temperature (° F.) | Pervaporative Cool (° F.) |
|---|---|---|---|---|---|
| Control #1 (PE) | None | None | 1.5 | 93.6 | — |
| Control #2 (PE) | None | None | 1.5 | 93.3 | — |
| X-7744 | 35 to 50% | 7 | 0.6 | 71.3 | 22.2 |
| X-6919 | 35 to 50% | <15 | 1.6 | 73.1 | 20.4 |
| 402HP | 40 to 45% | 40 | 0.6 | 73.1 | 20.4 |
| 402HP | 40 to 45% | 40 | 1.3 | 73.7 | 19.7 |
| Supported PTFE | 75% | >50 | 0.3 | 73.1 | 20.4 |

Table 1 sets forth endpoint water pervaporative cooling data at different ambient air velocities and the effect of a ¹⁄₁₆" open-cell porous urethane insulative matrix at a relative humidity of 30%. Tables 2 and 3 set forth endpoint water pervaporative cooling data at different relative humidities and in the dark or in the presence of direct solar irradiation. The pervaporative materials in all three tables are PTFE or sintered UHMWPE (ultra high molecular weight polyethylene).

Figure 9:
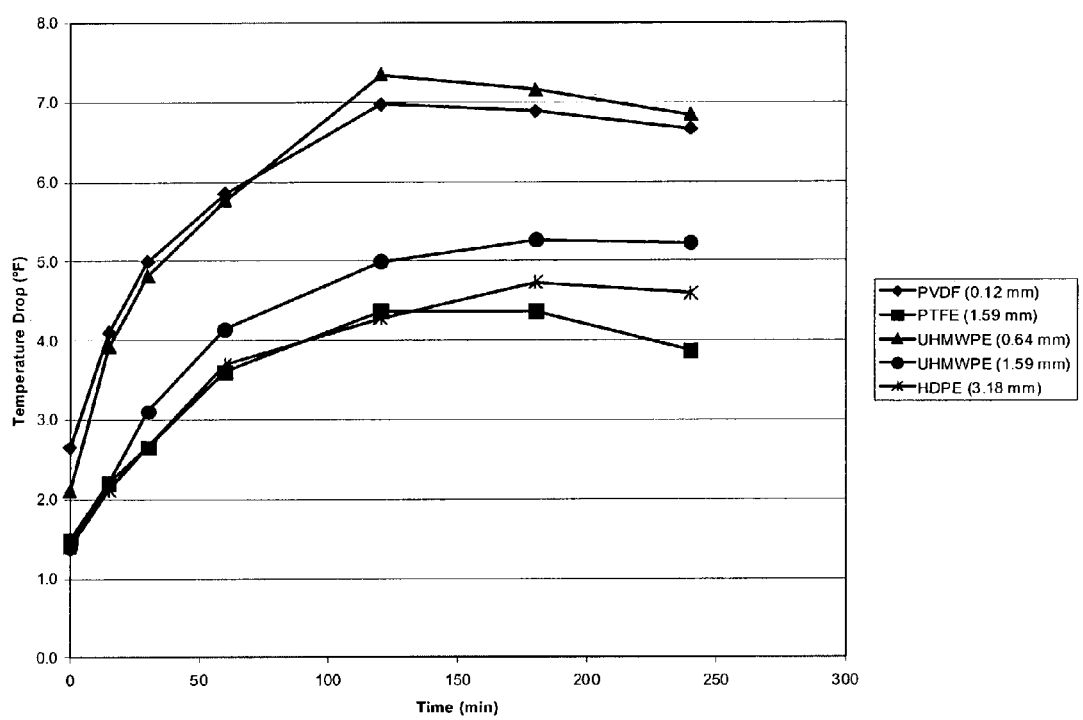
FIG. 9 is a graph of time versus cooling pertaining to pervaporative cooling equilibrium using a variety of porous matrices.

Additional enhancements in cooling efficiency may be seen with the container as the outside relative humidity drops and if the container is placed in direct sunlight. The lower external humidity increases the vapor concentration gradient, and the externally applied heat raises the liquid temperature and vapor pressure, which lead to a rise in the pervaporative flux. Depending on ambient conditions, the geometry and materials selection of the container, this process can maintain a sub-ambient cool in the container of 22° F. below ambient temperature. See Table 3. The time to attain this cooled temperature for a liquid volume of 700 ml is around 2 hours as demonstrated in FIG. 9 for a variety of pervaporative matrices and combinations thereof.

One preferred embodiment of evaporative cooling container includes a single or combined porous matrix having a pervaporative layer thickness of about 0.025 mm (0.001 in.) to 10 mm (0.394 in.). Additionally, to increase the efficiency of the pervaporative process, the matrix preferably has qualities such that it is minimally thermally conducting. It is preferable that the matrix does not substantially impede vapor diffusion, such that, in one embodiment, a pore size above about 100 nm is preferred. Preferred surface porosities of the matrix are between about 15 and 90% including about 20, 25, 30, 35, 40, 45, 50, 55, 60, 65, 70, 75, 80, and 85%. A porous matrix with a low thermal conductivity, such as a porous perfluorinated Styrofoam, an expanded porous matrix, or an open cell porous matrix made from hollow fused particles, can help to substantially prevent or reduce undue heat transfer from the surroundings into the container.

The various methods and techniques described above provide some of the numerous ways to carry out the invention. Of course, it is to be understood that not necessarily all objectives or advantages described may be achieved in accordance with any particular embodiment described herein or with any other single embodiment. Thus, for example, those skilled in the art will recognize that the methods may be performed and/or the articles made in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof.

What is claimed is:

1. A container for liquids comprising:
    a container body comprising one or more walls;
    wherein at least a portion of said one or more walls comprises a hydrophobic porous matrix that allows for the passage of vapor from a liquid within said container such that pervaporation or evaporation of said vapor cools said liquid within said container; and
    a regenerable or disposable outer layer directly adjacent to at least portion of said container body, said layer comprising a desiccant or an absorbent material that absorbs moisture or other fluid resulting from said evaporation or pervaporation.

2. A container for liquids according to claim 1 wherein said porous matrix comprises a membrane.

3. A container for liquids according to claim 1 wherein said porous matrix comprises a porous sintered matrix.

4. A container for liquids according to claim 1 wherein said porous matrix is fabricated from a polymer selected from the group consisting of polyethylenes, polypropylenes, ethylene copolymers, polymethylpentenes, polybutylenes, and blends thereof.

5. A container for liquids according to claim 1 wherein said porous matrix is fabricated from a polymer selected from the group consisting of polytetrafluoroethylene, polyvinylfluoride, polyvinylidinefluoride, polyethylenetetrafluoroethylene, fluorinated ethylene propylene, polyperfluoroalkoxyethylene, polyvinylchloride, chlorinatedpolyvinylchloride, polyvinyldichloride and blends thereof.

6. A container for liquids according to claim 1 wherein said porous matrix is fabricated from a blend of a fluorinated additive with a non-fluorinated plastic resin.

7. A container for liquids according to claim 1 wherein said porous matrix is fabricated from a silicone polymer or fluorosilicone polymer.

8. A container for liquids according to claim 1 wherein said porous matrix has a thickness of 0.025 to 7.0 mm.

9. A container for liquids according to claim 1 wherein said porous matrix has a thickness of 0.05 to 3.0 mm.

10. A container for liquids according to claim 1 wherein said porous matrix has a pore size of 0.05 to 500 μm.

11. A container for liquids according to claim 1 wherein said porous matrix has pore size of 0.1 to 100 μm.

12. A container for liquids according to claim 1 wherein said porous matrix has percent porosity of 10 to 90%.

13. A container for liquids according to claim 1 wherein said porous matrix has percent porosity of 30 to 70%.

14. A container for liquids according to claim 1 wherein said portion of said one or more walls is 5 to 100% of the total wall area of said container.

15. A container for liquids according to claim 1 wherein said porous matrix is comprised of hollow or expanded particles which are fused or adhered together to reduce the thermal conductivity of said porous matrix.

16. A container for liquids according to claim 1, wherein said hydrophobic porous matrix has a pleated structure.

17. A container for liquids comprising:
a container body comprising one or more walls;
wherein at least a portion of said one or more walls comprises a hydrophobic porous matrix that allows for the passage of vapor from a liquid within said container such that pervaporation or evaporation of said vapor cools said liquid within said container; and
an insulating sleeve surrounding at least a portion of said one or more walls.

18. A container for liquids according to claim 17 wherein said porous matrix comprises a membrane.

19. A container for liquids according to claim 17 wherein said porous matrix comprises a porous sintered matrix.

20. A container for liquids according to claim 17 wherein said porous matrix is fabricated from a polymer selected from the group consisting of polyethylenes, polypropylenes, ethylene copolymers, polymethylpentenes, polybutylenes, and blends thereof.

21. A container for liquids according to claim 17 wherein said porous matrix is fabricated from a polymer selected from the group consisting of polytetrafluoroethylene, polyvinylfluoride, polyvinylidinefluoride, polyethylenetetrafluoroethylene, fluorinated ethylene propylene, polyperfluoroalkoxyethylene, polyvinylchloride, chlorinatedpolyvinylchloride, polyvinyldichloride and blends thereof.

22. A container for liquids according to claim 17 wherein said porous matrix is fabricated from a blend of a fluorinated additive with a non-fluorinated plastic resin.

23. A container for liquids according to claim 17 wherein said porous matrix is fabricated from a silicone polymer or fluorosilicone polymer.

24. A container for liquids according to claim 17 wherein said porous matrix has a thickness of 0.025 to 7.0 mm.

25. A container for liquids according to claim 17 wherein said porous matrix has a thickness of 0.05 to 3.0 mm.

26. A container for liquids according to claim 17 wherein said porous matrix has a pore size of 0.05 to 500 μm.

27. A container for liquids according to claim 17 wherein said porous matrix has pore size of 0.1 to 100 μm.

28. A container for liquids according to claim 17 wherein said porous matrix has percent porosity of 10 to 90%.

29. A container for liquids according to claim 17 wherein said porous matrix has percent porosity of 30 to 70%.

30. A container for liquids according to claim 17 wherein said portion of said one or more walls is 5 to 100% of the total wall area of said container.

31. A container for liquids according to claim 17 wherein said porous matrix is comprised of hollow or expanded particles which are fused or adhered together to reduce the thermal conductivity of said porous matrix.

32. A container for liquids according to claim 17 wherein said porous matrix has a pleated structure.

33. A container for liquids according to claim 17 wherein said insulating sleeve comprises a porous insulative material.

34. A container for liquids according to claim 17, wherein said porous insulative material is open-cell porous insulative material.

35. A container for liquids according to claim 17, wherein said insulating sleeve is generally tubular and has one or more openings in the wall thereof, whereby the sleeve may be rotated about the container to selectively cover or expose portions of said porous matrix.

36. A container for liquids comprising:
a container body comprising one or more walls;
wherein at least a portion of said one or more walls comprises a porous matrix having a first surface and a second surface wherein said first surface is a hydrophobic surface and said second surface is a hydrophilic surface; and
wherein said porous matrix allows for the passage of vapor from a liquid within said container such that pervaporation or evaporation of said vapor cools said liquid within said container.

37. A container for liquids according to claim 36 wherein said porous matrix is oriented such that said hydrophilic surface faces the interior of the container.

38. A container for liquids according to claim 17 wherein said porous matrix comprises a porous hydrophilic membrane laminated to a porous hydrophobic membrane.

39. A container for liquids according to claim 17 wherein said second surface is rendered hydrophilic by a process selected from the group consisting of plasma etching, chemical etching, impregnation with wetting agents, and application of hydrophilic coatings.

40. A container for liquids according to claim 17 wherein said porous matrix has a thickness of 0.025 to 7.0 mm.

41. A container for liquids according to claim 17 wherein said porous matrix has a thickness of 0.05 to 3.0 mm.

42. A container for liquids according to claim 17 wherein said porous matrix has a pore size of 0.05 to 500 μm.

43. A container for liquids according to claim 17 wherein said porous matrix has pore size of 0.1 to 100 μm.

44. A container for liquids according to claim 17 wherein said porous matrix has percent porosity of 10 to 95%.

45. A container for liquids according to claim 17 wherein said porous matrix has percent porosity of 30 to 70%.

46. A container for liquids according to claim 17, wherein said portion of said one or more walls is 5 to 100% of the total wall area of said container.

47. A container for liquids according to claim 17 wherein said porous matrix has a pleated structure.

* * * * *

UNITED STATES PATENT AND TRADEMARK OFFICE
CERTIFICATE OF CORRECTION

PATENT NO. : 7,107,783 B2
APPLICATION NO. : 10/453863
DATED : September 19, 2006
INVENTOR(S) : Daniel D. Smolko and Gregory J. Kevorkian Page 1 of 1

It is certified that error appears in the above-identified patent and that said Letters Patent is hereby corrected as shown below:

On the title page item (73) Assignee: Advanced "Porcus" Technologies, LLC should read (73) Assignee: Advanced --Porous-- Technologies, LLC Signed and Sealed this Twenty-third Day of June, 2009

JOHN DOLL
*Acting Director of the United States Patent and Trademark Office*